United States Patent
Hurd et al.

(10) Patent No.: US 9,713,440 B2
(45) Date of Patent: Jul. 25, 2017

(54) MODULAR ANALYTE MEASUREMENT SYSTEMS, MODULAR COMPONENTS THEREOF AND RELATED METHODS

(75) Inventors: Marsha Kaye Hurd, Clayton, CA (US); Michael Isherwood, San Francisco, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 171 days.

(21) Appl. No.: 13/298,021

(22) Filed: Nov. 16, 2011

(65) Prior Publication Data

US 2012/0150448 A1 Jun. 14, 2012

Related U.S. Application Data

(60) Provisional application No. 61/421,122, filed on Dec. 8, 2010.

(51) Int. Cl.
| | | |
|---|---|---|
| C12M 1/00 | (2006.01) | |
| H04Q 1/30 | (2006.01) | |
| A61B 5/145 | (2006.01) | |
| G06F 19/00 | (2011.01) | |
| A61B 5/00 | (2006.01) | |

(52) U.S. Cl.
CPC ........ *A61B 5/14532* (2013.01); *A61B 5/0022* (2013.01); *A61B 2560/0443* (2013.01); *G06F 19/3468* (2013.01); *Y10T 29/49002* (2015.01)

(58) Field of Classification Search
None
See application file for complete search history.

(56) References Cited

U.S. PATENT DOCUMENTS

| | | |
|---|---|---|
| 4,150,863 A | 4/1979 | Krafthefer et al. |
| 4,494,809 A | 1/1985 | Soloman |
| | (Continued) | |

FOREIGN PATENT DOCUMENTS

| | | |
|---|---|---|
| DE | 202006013075 | 11/2006 |
| EP | 1112717 | 7/2001 |
| | (Continued) | |

OTHER PUBLICATIONS

International Search Report for PCT Application No. PCT/US2009/050119, dated Jan. 18, 2010.

(Continued)

*Primary Examiner* — Anna Skibinsky
(74) *Attorney, Agent, or Firm* — Edward J. Baba; Brian E. Davy; Bozicevic, Field & Francis LLP

(57) ABSTRACT

Presented herein is a modular analyte measurement system having a replaceable strip port module that releasably connects and operably couples with an analyte meter. Embodiments of the present invention also relate to modular components of the analyte measurement system. In one aspect, there is provided a replaceable strip port module having a strip port and electrical interface for removably and electrically coupling with an analyte meter. In another aspect, there is provided an analyte meter that includes a processor and electrical interface for removably and electrically coupling with replaceable strip port modules. Methods of configuring the analyte measurement system and methods of determining an analyte meter with the analyte measurement system are also provided.

25 Claims, 12 Drawing Sheets

(56) References Cited

U.S. PATENT DOCUMENTS

| | | |
|---|---|---|
| 4,533,202 A | 8/1985 | Pohl |
| 4,545,382 A | 10/1985 | Higgins et al. |
| 4,711,245 A | 12/1987 | Higgins et al. |
| 4,774,192 A | 9/1988 | Terminiello et al. |
| 4,868,711 A | 9/1989 | Hirama et al. |
| 4,911,344 A | 3/1990 | Kahler |
| 4,940,422 A | 7/1990 | Forish et al. |
| 5,217,388 A | 6/1993 | Brown |
| 5,262,035 A | 11/1993 | Gregg et al. |
| 5,262,305 A | 11/1993 | Heller et al. |
| 5,264,014 A | 11/1993 | Lannefors et al. |
| 5,279,294 A | 1/1994 | Anderson et al. |
| 5,282,950 A | 2/1994 | Dietze et al. |
| 5,320,715 A | 6/1994 | Berg |
| 5,356,786 A | 10/1994 | Heller et al. |
| 5,366,609 A * | 11/1994 | White ............ G01N 33/48792 204/403.04 |
| 5,391,094 A | 2/1995 | Kakinoki et al. |
| 5,509,410 A | 4/1996 | Hill et al. |
| 5,526,120 A | 6/1996 | Jina et al. |
| 5,536,249 A | 7/1996 | Castellano et al. |
| D376,763 S | 12/1996 | Flora et al. |
| 5,593,323 A | 1/1997 | Dernehl |
| 5,593,852 A | 1/1997 | Heller et al. |
| 5,601,435 A | 2/1997 | Quy |
| 5,628,890 A | 5/1997 | Carter et al. |
| 5,705,936 A | 1/1998 | Gibson et al. |
| 5,708,247 A | 1/1998 | McAleer et al. |
| 5,820,551 A | 10/1998 | Hill et al. |
| 5,822,715 A | 10/1998 | Worthington et al. |
| 5,899,855 A | 5/1999 | Brown |
| 5,918,603 A | 7/1999 | Brown |
| 5,925,021 A | 7/1999 | Castellano et al. |
| D413,537 S | 9/1999 | Grossman et al. |
| 5,984,690 A | 11/1999 | Riechelmann et al. |
| 6,071,391 A | 6/2000 | Gotoh et al. |
| 6,120,676 A | 9/2000 | Heller et al. |
| 6,121,009 A | 9/2000 | Heller et al. |
| 6,143,164 A | 11/2000 | Heller et al. |
| 6,144,837 A | 11/2000 | Quy |
| 6,161,095 A | 12/2000 | Brown |
| 6,175,752 B1 | 1/2001 | Say et al. |
| 6,183,274 B1 | 2/2001 | Allum |
| 6,268,162 B1 | 7/2001 | Phillips et al. |
| 6,270,455 B1 | 8/2001 | Brown |
| 6,281,006 B1 | 8/2001 | Heller et al. |
| 6,284,478 B1 | 9/2001 | Heller et al. |
| 6,299,757 B1 | 10/2001 | Feldman et al. |
| 6,338,790 B1 | 1/2002 | Feldman et al. |
| 6,377,894 B1 | 4/2002 | Deweese et al. |
| 6,431,884 B1 | 8/2002 | Wallace et al. |
| 6,445,350 B2 | 9/2002 | Takenobu |
| 6,461,496 B1 | 10/2002 | Feldman et al. |
| 6,503,381 B1 | 1/2003 | Gotoh et al. |
| 6,506,168 B1 | 1/2003 | Fathallah et al. |
| 6,514,460 B1 | 2/2003 | Fendrock |
| 6,514,718 B2 | 2/2003 | Heller et al. |
| 6,540,891 B1 | 4/2003 | Stewart et al. |
| 6,560,471 B1 | 5/2003 | Heller et al. |
| 6,591,125 B1 | 7/2003 | Buse et al. |
| 6,592,745 B1 | 7/2003 | Feldman et al. |
| 6,600,997 B2 | 7/2003 | Deweese et al. |
| 6,616,819 B1 | 9/2003 | Liamos et al. |
| 6,618,934 B1 | 9/2003 | Feldman et al. |
| 6,638,716 B2 | 10/2003 | Heller et al. |
| 6,676,816 B2 | 1/2004 | Mao et al. |
| 6,679,137 B1 | 1/2004 | Bek |
| 6,730,200 B1 | 5/2004 | Stewart et al. |
| 6,736,957 B1 | 5/2004 | Forrow et al. |
| 6,743,635 B2 | 6/2004 | Neel et al. |
| 6,746,582 B2 | 6/2004 | Heller et al. |
| 6,749,740 B2 | 6/2004 | Liamos et al. |
| 6,764,581 B1 | 7/2004 | Forrow et al. |
| 6,773,671 B1 | 8/2004 | Lewis et al. |
| 6,850,283 B1 | 2/2005 | Tatamiya |
| 6,881,551 B2 | 4/2005 | Heller et al. |
| 6,881,578 B2 | 4/2005 | Otake |
| 6,893,545 B2 | 5/2005 | Gotoh et al. |
| 6,908,008 B2 | 6/2005 | Pugh |
| 6,940,021 B2 | 9/2005 | Pohl et al. |
| 6,942,518 B2 | 9/2005 | Liamos et al. |
| 6,976,624 B2 | 12/2005 | Hsiao |
| 7,041,468 B2 | 5/2006 | Drucker et al. |
| 7,077,328 B2 | 7/2006 | Krishnaswamy et al. |
| 7,167,818 B2 | 1/2007 | Brown |
| 7,172,728 B2 | 2/2007 | Otake |
| 7,179,129 B1 | 2/2007 | Hwang |
| D540,208 S | 4/2007 | Mobley et al. |
| 7,299,082 B2 | 11/2007 | Feldman et al. |
| D560,129 S | 1/2008 | Rich et al. |
| 7,337,918 B2 | 3/2008 | Fowler et al. |
| 7,488,216 B2 | 2/2009 | Cho |
| 7,866,026 B1 | 1/2011 | Wang et al. |
| 7,896,703 B2 | 3/2011 | Stafford et al. |
| 8,292,180 B2 | 10/2012 | Ehrhart et al. |
| 8,292,810 B2 | 10/2012 | Goode et al. |
| 8,301,395 B2 | 10/2012 | Matievich et al. |
| 8,328,735 B2 | 12/2012 | Haar et al. |
| 2002/0117639 A1 * | 8/2002 | Paolini et al. ............. 250/559.1 |
| 2003/0050537 A1 | 3/2003 | Wessel |
| 2003/0176183 A1 | 9/2003 | Drucker et al. |
| 2003/0191415 A1 | 10/2003 | Moerman et al. |
| 2004/0073095 A1 | 4/2004 | Causey et al. |
| 2004/0086425 A1 | 5/2004 | Jaunakais |
| 2004/0094433 A1 | 5/2004 | Neel et al. |
| 2004/0186365 A1 | 9/2004 | Jin et al. |
| 2004/0254434 A1 | 12/2004 | Goodnow et al. |
| 2004/0267300 A1 | 12/2004 | Mace |
| 2005/0121826 A1 | 6/2005 | Hajizadeh et al. |
| 2005/0154271 A1 | 7/2005 | Rasdal et al. |
| 2005/0169810 A1 | 8/2005 | Hagen et al. |
| 2005/0239156 A1 | 10/2005 | Drucker et al. |
| 2005/0281706 A1 | 12/2005 | Funke et al. |
| 2006/0025662 A1 | 2/2006 | Buse et al. |
| 2006/0030789 A1 | 2/2006 | Allen |
| 2006/0040333 A1 | 2/2006 | Zocchi |
| 2006/0091006 A1 | 5/2006 | Wang et al. |
| 2006/0148096 A1 | 7/2006 | Jina |
| 2006/0224141 A1 | 10/2006 | Rush et al. |
| 2007/0015983 A1 * | 1/2007 | Werner et al. ............... 600/347 |
| 2007/0068807 A1 | 3/2007 | Feldman et al. |
| 2007/0095661 A1 | 5/2007 | Wang et al. |
| 2007/0100222 A1 | 5/2007 | Mastrototaro et al. |
| 2007/0108048 A1 | 5/2007 | Wang et al. |
| 2007/0149897 A1 | 6/2007 | Ghesquiere et al. |
| 2007/0199818 A1 | 8/2007 | Petyt et al. |
| 2007/0233395 A1 | 10/2007 | Neel et al. |
| 2007/0247793 A1 | 10/2007 | Carnevali |
| 2008/0066305 A1 | 3/2008 | Wang et al. |
| 2008/0099332 A1 | 5/2008 | Scott et al. |
| 2008/0102441 A1 | 5/2008 | Chen et al. |
| 2008/0119709 A1 | 5/2008 | Wang et al. |
| 2008/0148873 A1 | 6/2008 | Wang |
| 2008/0167578 A1 | 7/2008 | Bryer et al. |
| 2008/0188732 A1 * | 8/2008 | Mace et al. .................. 600/347 |
| 2008/0234559 A1 | 9/2008 | Arbogast et al. |
| 2008/0267823 A1 | 10/2008 | Wang et al. |
| 2008/0269673 A1 | 10/2008 | Butio et al. |
| 2009/0018411 A1 | 1/2009 | Mace et al. |
| 2009/0095625 A1 | 4/2009 | Forrow et al. |
| 2009/0117861 A1 | 5/2009 | Hoefel et al. |
| 2009/0187351 A1 | 7/2009 | Orr et al. |
| 2009/0255811 A1 | 10/2009 | Forrow et al. |
| 2009/0270696 A1 | 10/2009 | Arbogast et al. |
| 2010/0015649 A1 | 1/2010 | Day |
| 2010/0015860 A1 | 1/2010 | Stafford et al. |
| 2010/0064800 A1 | 3/2010 | Stafford et al. |
| 2010/0198034 A1 | 8/2010 | Thomas et al. |
| 2010/0198142 A1 | 8/2010 | Sloan et al. |
| 2010/0213057 A1 | 8/2010 | Feldman et al. |
| 2010/0324392 A1 | 12/2010 | Yee et al. |
| 2010/0326842 A1 | 12/2010 | Mazza et al. |
| 2010/0331652 A1 | 12/2010 | Groll et al. |

(56) References Cited

U.S. PATENT DOCUMENTS

| | | |
|---|---|---|
| 2011/0040246 A1 | 2/2011 | Galasso |
| 2011/0184264 A1 | 7/2011 | Galasso et al. |
| 2012/0100601 A1 | 4/2012 | Simmons et al. |

FOREIGN PATENT DOCUMENTS

| | | |
|---|---|---|
| EP | 1543935 | 6/2005 |
| EP | 1712910 | 10/2006 |
| EP | 1729128 | 12/2006 |
| FR | 2674379 | 9/1992 |
| GB | 1170256 | 11/1969 |
| JP | 2-220375 | 9/1990 |
| JP | H07-240251 | 9/1995 |
| JP | 2000326359 | 11/2000 |
| JP | 2004020367 | 1/2004 |
| KR | 20060119039 | 11/2006 |
| WO | WO 2005096446 | 10/2005 |
| WO | WO 2006002432 | 1/2006 |
| WO | WO 2007097746 | 8/2007 |

OTHER PUBLICATIONS

International Search Report for PCT Application No. PCT/US2011/057741, dated Mar. 6, 2012.

\* cited by examiner

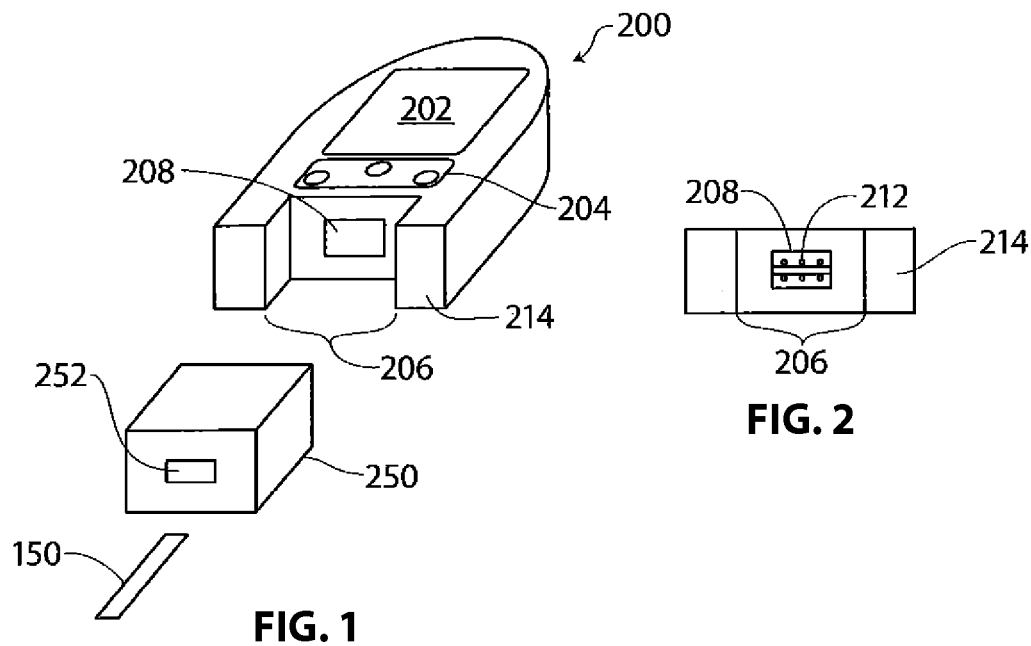
FIG. 1
FIG. 2
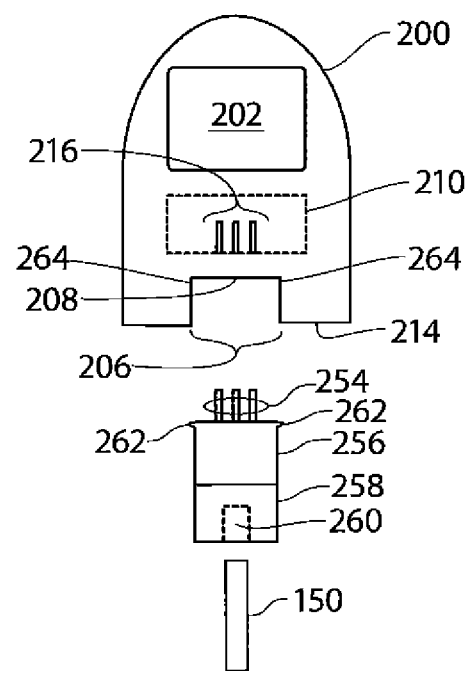
FIG. 3

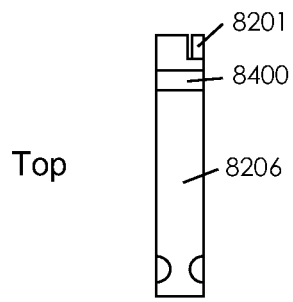
FIG. 15A
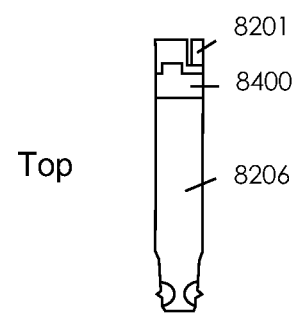
FIG. 15B
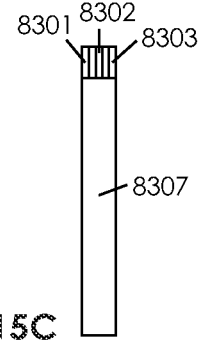
FIG. 15C
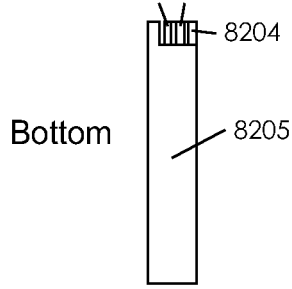
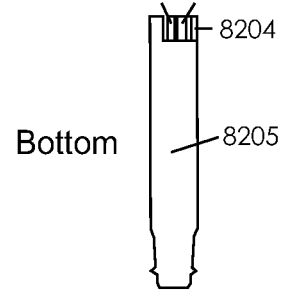
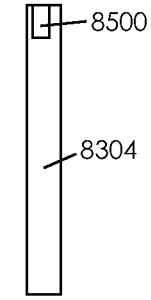
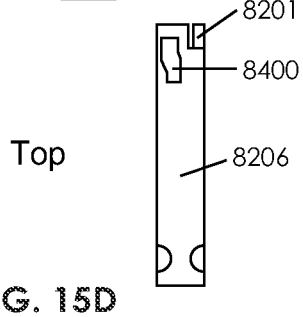
FIG. 15D
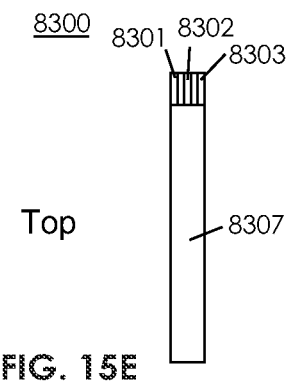
FIG. 15E
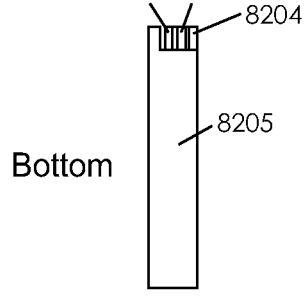
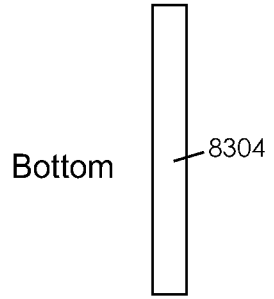

MODULAR ANALYTE MEASUREMENT SYSTEMS, MODULAR COMPONENTS THEREOF AND RELATED METHODS

CROSS-REFERENCE TO RELATED APPLICATIONS

This application claims the benefit of U.S. Provisional Application No. 61/421,122, filed on Dec. 8, 2010, which is herein incorporated by reference in its entirety.

BACKGROUND

One of the tools used in diabetes management is an analyte measurement device (or analyte meter). An analyte measurement device is typically used to measure the analyte level (e.g., glucose level) of a person based on a sample of blood. The process of using an analyte measurement device is not complicated, and is often performed several times a day. First, a user inserts an analyte test strip into a strip port of the measurement device. The user then lances her finger to obtain a small sample of blood. The blood sample is then placed onto the analyte test strip, and the measurement device analyzes the blood sample to determine the concentration of the analyte in the blood. The measurement device then typically displays the analyte level (e.g., blood glucose level) from the analysis.

In order to ensure an accurate measurement is being generated, it is necessary to keep the measurement device free from contamination. There are instances where the strip port may become contaminated—e.g., with dirt, control solution, bodily fluids such as blood, other fluids such as calibration fluid, etc. When this occurs, the performance of the measurement device suffers and the user is no longer assured an accurate result or will no longer work. As such, the user may need to purchase a new measurement device even though the rest of the high value components of the meter are fully functional.

Dedicated hospital meters have high occurrence rates of contamination due to factors such as heavy use, need for calibration, and other environmental factors. Contamination of a hospital meter, and the subsequent need to replace the hospital meter, is costly. Further, the inventors have found that a substantial number of hospital meters are returned to the manufacturer simply because the strip port has been contaminated, while most of the other parts of the meter remain entirely functional.

Furthermore, if users have a meter that is configured to do one type of measurement—e.g., have a strip port with a specific form factor and/or testing technique implemented—and they want to perform a different type of measurement—e.g., requiring a different strip port form factor and/or testing technique—then the user is unable to perform the measurement unless acquiring a different meter. Such users will have to purchase multiple meters, which can be costly.

BRIEF SUMMARY

Presented herein is a modular analyte measurement system having a replaceable strip port module that releasably connects and operably couples with an analyte meter. Embodiments of the present invention also relate to modular components of the analyte measurement system. In one aspect, there is provided a replaceable strip port module having a strip port and electrical interface for removably and electrically coupling with an analyte meter. In another aspect, there is provided an analyte meter that includes a processor and electrical interface for removably and electrically coupling with replaceable strip port modules. Methods of configuring the analyte measurement system and methods of determining an analyte meter with the analyte measurement system are also provided.

BRIEF DESCRIPTION OF THE FIGURES

The accompanying drawings, which are incorporated herein, form part of the specification. Together with this written description, the drawings further serve to explain the principles of, and to enable a person skilled in the relevant art(s), to make and use the present invention.

FIG. 1 illustrates a perspective view of a device that uses a disposable strip port, according to certain embodiments.

FIG. 2 illustrates a side view of an end of the device including the electrical interface that receives the replaceable strip port module, according to certain embodiments.

FIG. 3 illustrates a top view of a replaceable strip port module that interfaces with a device and with a test strip, according to certain embodiments.

FIGS. 15A-15E illustrates analyte test strips having various electrode configurations, according to certain embodiments.

DETAILED DESCRIPTION OF THE INVENTION

Figure 4:
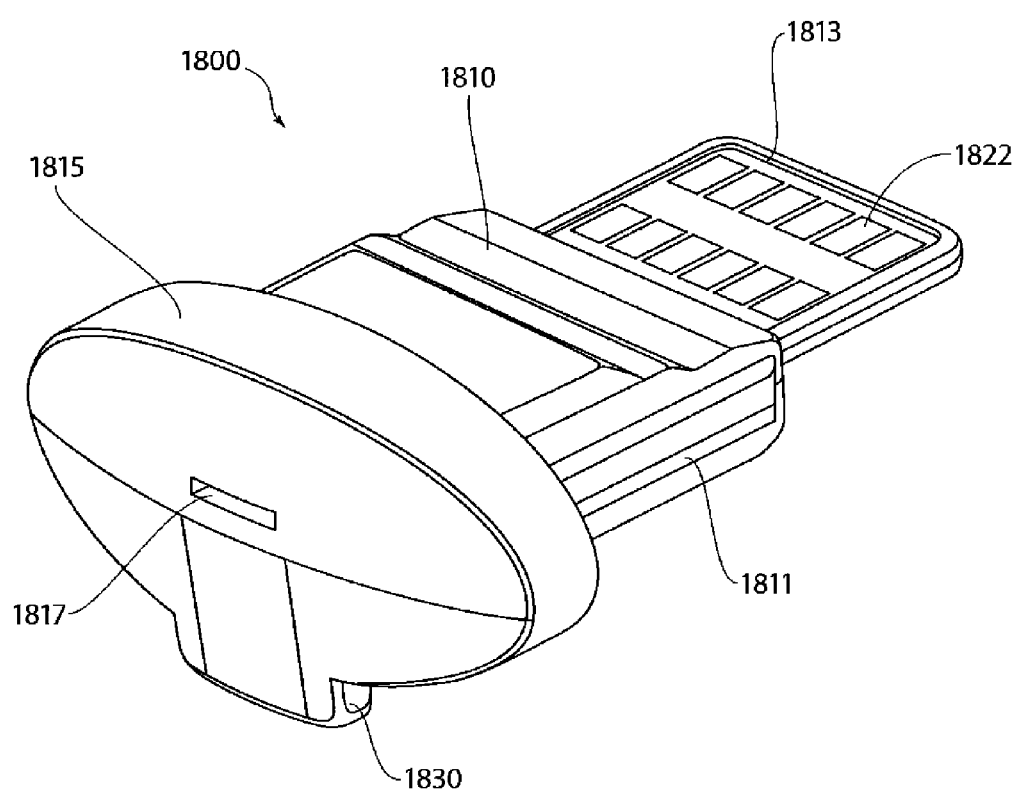
FIG. 4 illustrates a front-side perspective view of a replaceable strip port module, according to certain embodiments.

Before the embodiments of the present disclosure are described, it is to be understood that this invention is not limited to particular embodiments described, as such may, of course, vary. It is also to be understood that the terminology used herein is for the purpose of describing particular embodiments only, and is not intended to be limiting, since the scope of the embodiments of the invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

In the description of the invention herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described below to facilitate an understanding of the invention. It will be understood that a corresponding description of these various terms applies to corresponding linguistic or grammatical variations or forms of these various terms. It will also be understood that the invention is not limited to the terminology used herein, or the descriptions thereof, for the description of particular embodiments. Merely by way of example, the invention is not limited to particular analytes, bodily or tissue fluids, blood or capillary blood, or sensor constructs or usages, unless implicitly or explicitly understood or stated otherwise, as such may vary.

The publications discussed herein are provided solely for their disclosure prior to the filing date of the application. Nothing herein is to be construed as an admission that the embodiments of the invention are not entitled to antedate such publication by virtue of prior invention. Further, the dates of publication provided may be different from the actual publication dates which may need to be independently confirmed.

The following detailed description of the figures refers to the accompanying drawings that illustrate exemplary embodiments of analyte measurement systems, modular components thereof, and related methods thereof. Other embodiments are possible. Modifications may be made to the embodiments described herein without departing from the spirit and scope of the present invention. Therefore, the following detailed description is not meant to be limiting.

Embodiments presented herein relate to replaceable strip port modules that can be disposed of and replaced. The ability to replace a strip port can prevent the device from experiencing problems often associated with port contamination. Blood and other contaminants, for example, can often contaminate a port and make the device unusable or result in inaccurate analysis. In some embodiments, the replaceable strip port module may also be disconnected from the analyte meter and cleaned to prolong the life of the replaceable strip port module and meter. Therefore, a replaceable strip port module can be cleaned or replaced without affecting the operation of the meter, and thus increases the mean time between failures, for example.

It should also be appreciated that the replaceable strip port modules also enable different types of replaceable strip port modules to be connected to the same analyte meter. Therefore, in some instances, the replaceable strip port modules may be replaced with a different type of replaceable strip port module and not necessarily disposed of at that time. Different types of replaceable strip port modules are discussed in further detail below, and may vary, for example, based on form factor and testing techniques implemented.

Embodiments presented herein, thus may provide various advantages such as: the ability to upgrade strip port modules as new test strip technologies evolve; the ability to clean or sterilize a strip port module; and the ability to allow users to replace strip port modules without returning the entire measurement system to the manufacture or disposing of the entire measurement system.

In some aspects, a modular analyte measurement system having a replaceable strip port module is provided. The replaceable strip port module releasably connects and operably couples with an analyte meter. In certain embodiments, the analyte meter is not fully operable as an analyte meter without the connection of the replaceable strip port module. For example, the replaceable strip port module includes a strip port that the analyte meter requires to perform a measurement on an analyte test strip. Some aspects of the present disclosure also relate to modular components of the analyte measurement system. In some aspects, there is provided a replaceable strip port module having a strip port and electrical interface for removably and electrically coupling with an analyte meter. When connected, the replaceable strip port module is configured to indicate to the analyte meter that it is connected. The replaceable strip port module may also be configured to indicate to the analyte meter the type of replaceable strip port module that is connected and/or what type of analyte is to be measured. In some aspects, there is provided an analyte meter that includes a processor and electrical interface for removably and electrically coupling with replaceable strip port modules. The analyte meter receives an indication from the replaceable strip port module as to when a replaceable strip port module is connected. It may also be configured to receive an indication from the replaceable strip port module as to what type of replaceable strip port module is connected and/or what type of analyte is to be measured. Methods of configuring the analyte measurement system and methods of determining an analyte meter with the analyte measurement system are also provided.

As stated above, in some aspects of the present disclosure a replaceable strip port module is provided. The replaceable strip port module may be, for example, disposable so that it may be disposed of after it stops functioning properly—e.g., after it becomes contaminated. A replaceable strip port module enables the replaceable strip port module or a portion thereof to be exchanged, by way of example and not limitation, for another replaceable strip port module or portion thereof when the current replaceable strip port module or portion thereof malfunctions or is contaminated. FIG. 1 illustrates a perspective view of a measurement device 200 (e.g., an analyte meter). The device 200 includes a display 202 and a user interface 204. The display 202 may be used to convey information including results (such as blood glucose level) on an analysis of an analyte such as a blood sample. The user interface 104 allows a user to perform various functions, including starting the analysis, turning the device on/off, and the like.

The device 200 includes a port 208 that is inset in a receptacle 206 formed in the device 200. The receptacle 206 can be configured to receive a replaceable strip port module 250. As illustrated in FIG. 1, the replaceable strip port module 250 can be inserted into the receptacle 206 and connected both physically and electrically with the device 200 through the port 208. The replaceable strip port module 250 includes a strip port 252 that is configured to receive the test strip 150. When the replaceable strip port module 250 is inserted into the receptacle 206, the surface with the port 252 is often flush with the surface 214, although other configurations are possible with respect to the position of the replaceable strip port module 250 relative to the device 200. An electrical interface on the device 200 removably and electrically couples with an electrical interface on the replaceable strip port module 250 to enable electrical communication between the strip port module 250 and meter device 200. It should be appreciated that the electrical communication may be one or two way communication in different embodiments.

FIG. 2 illustrates a view of an end of the device 200. FIG. 2 illustrates that port 208 and the printed circuit board 212 (or other suitable interface) are disposed therein at the end of the receptacle 206. The printed circuit board 212 may have traces 216 or other contacts on either side of the printed circuit board 212 that form part of the electrical interface on the meter.

In some embodiments, replaceable strip port module may be configured to include two portions that may be repeatedly separated and connected. FIG. 3 illustrates a top view of the device 200, the replaceable strip port module 250, and a test strip 150. In this example, the port 208 provides access to the contacts 216 of the printed circuit board 212. The replaceable strip port module 250 also includes corresponding contacts 254 that are configured to connect with the traces 216. The contacts 254 may be spring arms, pins, and the like or any combination thereof. Further, in some instances, the port 208 may be insert molded to provide an interface that is substantially impervious to contaminants. In this case, the port may be changeable to allow the device 200 to adapt to different form factors or to provide other functions according to the configuration of the replaceable strip port module 250.

In this example, the replaceable strip port module 250 also has a strip receptacle 260 (an example of the strip port 252) or strip port disposed on a side opposite the contacts 254, although the receptacle can be repositioned on any side of the replaceable strip port module 250. The test strip 150 may be inserted into the receptacle 260 and a sample of the test strip 150 may be analyzed when the replaceable strip port module 250 is connected to the port 208.

The replaceable strip port module 250 in this example includes a first portion 256 and a second portion 258. The portion 256 and the portion 258 may be repeatedly separated and connected. As previously mentioned, the portion 258 can be replace with differently configured portions to provide a receptacle 260 that accommodates different test strip form factors.

The portion 256 may be configured to interface with the device 200 via the port 208. The portion 256 may also include retention tabs 262 that interact with corresponding connectors 264 to connect at least the portion 256 with the device 200 physically. In one example, the portion 256 may permanently connect with the device 200, while allowing the portion 258 to be disposable. Advantageously, a user can select differently configured portions 258 to adapt to different configurations of the test strips. This may allow a user not only to replace the replaceable strip port module 250 or a portion thereof, but also utilize test strips of different form factors. It should be appreciated that the replaceable strip port module and analyte meter may include other various engagement features that releasably connect the two devices.

Additional details regarding replaceable strip port modules, their mechanical structures and configuration, and example embodiments may be found in U.S. Provisional Patent Application No. 61/406,860 entitled "Modular Analyte Measurement System", filed on Oct. 26, 2010, which is incorporated by reference herein in its entirety.

Figure 5:
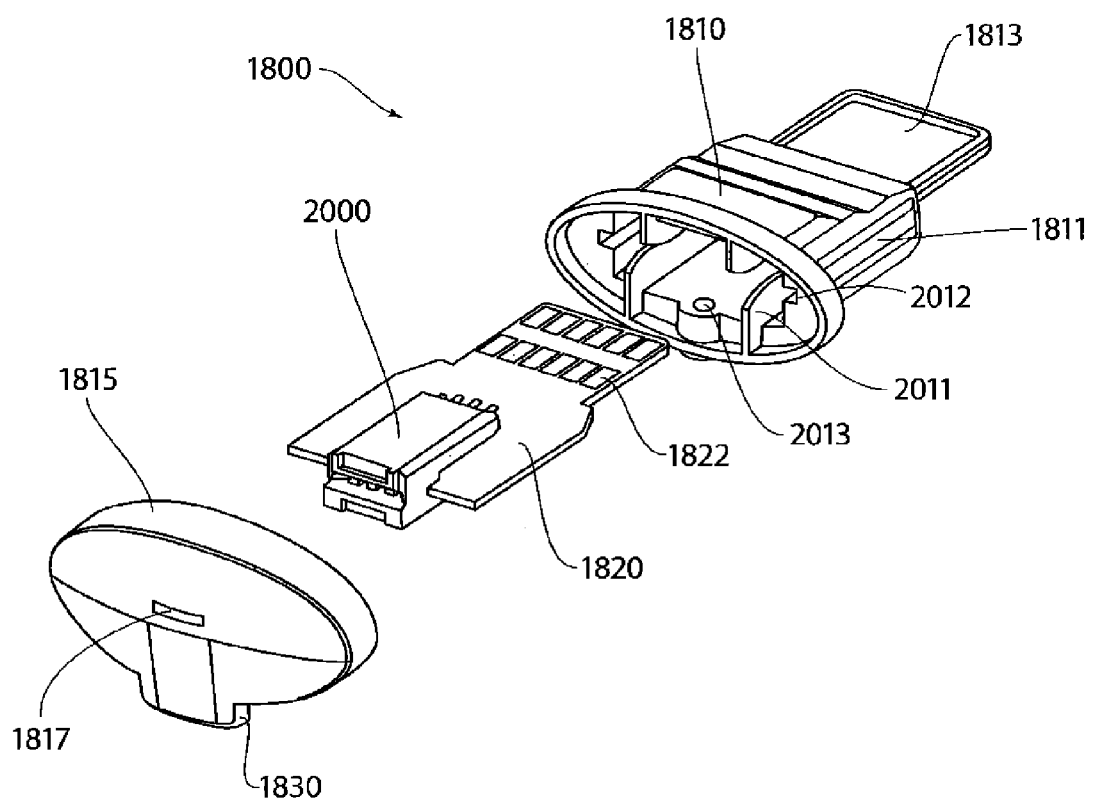
FIG. 5 illustrates an exploded view of the replaceable strip port module of FIG. 4, showing the internal components of the replaceable strip port module, according to certain embodiments.

FIGS. 4 and 5 provide different views of a replaceable strip port module 1800, in accordance with another embodiment presented herein. For example, FIG. 4 is a front-side perspective view of replaceable strip port module 1800, and FIG. 5 is an exploded view of replaceable strip port module 1800.

As shown in FIGS. 4 and 5, replaceable strip port module 1800 includes a housing 1810 with a cap 1815. An analyte test strip port 2000 is disposed within an open end of housing 1810, which is then enclosed (or covered) by cap 1815. In one embodiment, analyte test strip port 2000 is an electro-chemical strip port. In an alternative embodiment, analyte test strip port 2000 is an optical strip port. As shown in FIG. 5, analyte test strip port 2000 is coupled to a printed circuit board (PCB) 1820, and electrical leads of analyte test strip port 2000 are electrically coupled to one or more contact pads 1822 on PCB 1820. Housing 1810 includes an interface portion (or interface aperture) 1813 to expose contact pads 1822 when analyte test strip port 2000 and PCB 1820 are inserted and aligned within housing 1810. In one embodiment, a seal member may be provided along the edge of interface aperture 1813 to provide a fluid tight seal between PCB 1820 and housing 1810.

In one embodiment, housing 1810 is formed of a plastic mold, and more preferably an anti-microbial plastic mold. In alternative embodiments, housing 1810 may be formed of other suitable materials such as rubbers, polymers, or thermally conductive materials. In one embodiment, for example, housing 1810 and internal components is formed of medical grade PC/ABS plastic blend, and may include an anti-microbial plastic such as BAYER BAYBLEND AM120FR. In the embodiment shown in FIG. 5, housing 1810 includes internal alignment features, such as internal alignment baffles 2011 and internal alignment grooves 2012, to properly align analyte test strip port 2000 and PCB 1820 within housing 1810. Such internal alignment features, and structures equivalent thereto, serve as means for aligning an analyte test strip port within the module housing. A screw hole 2013 is provided in housing 1810 to attach replaceable strip port module 1800 to an analyte meter, as further discussed below. A screw for use in screw hole 2013 may be a stainless steel, pan head Philips, thread-forming screw.

Housing 1810 also includes external alignment features or guides 1811 and beveled surfaces to further support the proper insertion and alignment of replaceable strip port module 1800 within an analyte meter. Such external alignment features, and structures equivalent thereto, serve as means for aligning a replaceable strip port module within an analyte meter.

Cap 1815 serves to fully encase analyte test strip port 2000 within housing 1810. In one embodiment, cap 1815 is permanently attached to housing 1810 with a hermetic seal. In an alternative embodiment, cap 1815 may be removably attached to housing 1810. In another alternative embodiment, a gasket means (e.g., a rubber o-ring, fabric, etc.) may be used to seal the gap between cap 1815 and housing 1810. In the embodiment shown, cap 1815 also includes an optional tab extension 1830 to facilitate in the insertion and removal of replaceable strip port module 1800 from an analyte meter.

Cap 1815 further includes an aperture 1817, which provides access to analyte test strip port 2000. In operation, an analyte test strip is inserted through aperture 1817 and into analyte test strip port 2000. In one embodiment, aperture 1817 provides sufficient clearance to accept a wide variety of different analyte test strips form factors. In an alternative embodiment, aperture 1817 may be customized to receive a specific analyte test strip form factor. Customizing the aperture size or shape to a specific analyte test strip form factor can prevent the use of non-matching or incompatible analyte test strips with analyte test strip port 2000. Aperture 1817 may also be formed with a one-way valve or port protector to swipe across the surface of an analyte test strip when the analyte test strip is passed through aperture 1817. Such an embodiment may be used to protect analyte test strip port 2000 from unwanted contaminants. In alternative embodiments, aperture 1817 may incorporate one or more port protectors, such as disclosed in U.S. Patent Application Publication No. 2009/0270696, which is incorporated by reference herein in its entirety.

Figure 6:
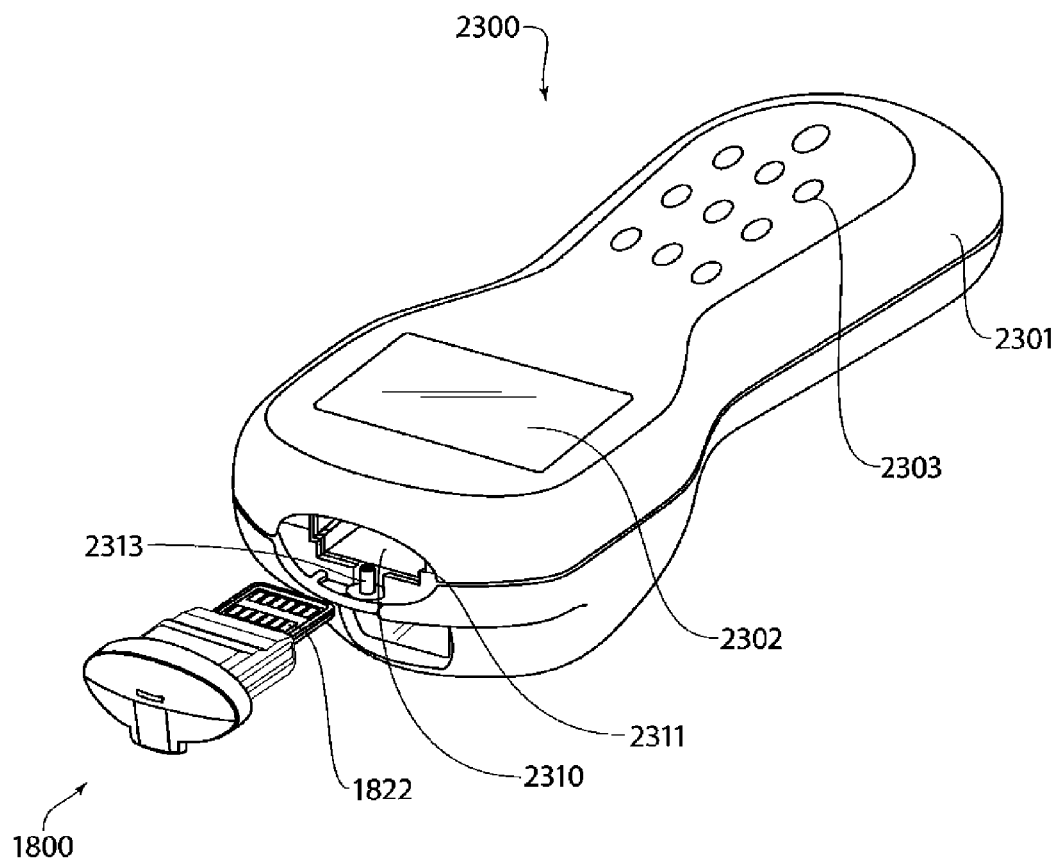
FIG. 6 illustrates a perspective view of a modular analyte measurement system, according to certain embodiments.
Figure 7:
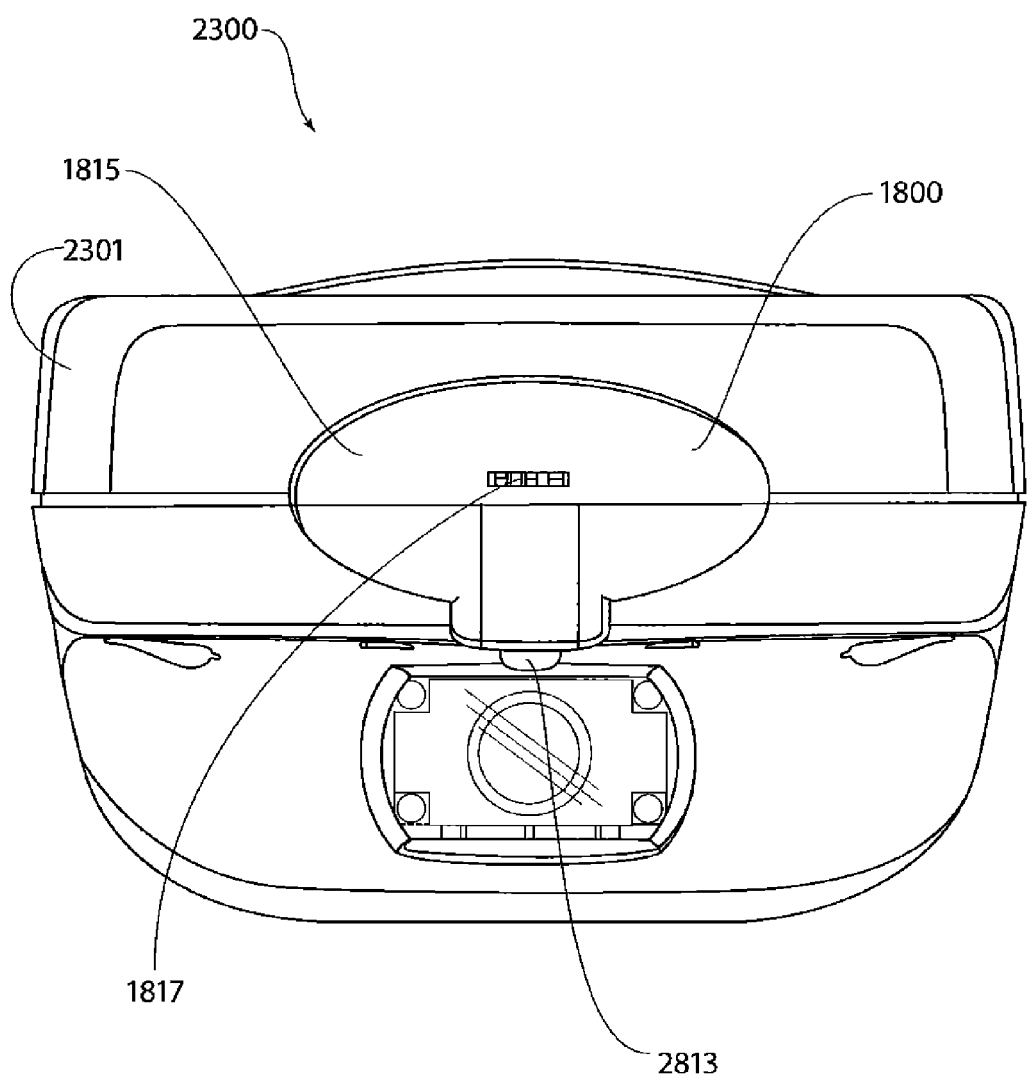
FIG. 7 illustrates a front-side view of the embodiment shown in FIG. 6, according to certain embodiments.

FIGS. 6 and 7 illustrate different views of a modular analyte measurement system 2300, including a replaceable strip port module, such as replaceable strip port module 1800, and an analyte meter 2301. For example, FIG. 6 is a perspective view of system 2300 prior to insertion of replaceable strip port module 1800 into analyte meter 2301. FIG. 7 is a front view of system 2300 having replaceable strip port module 1800 inserted into analyte meter 2301.

Analyte meter 2301 may be similar to analyte meters known in the art. For example, analyte meter 2301 may include similar structures, functions, and components as the analyte meters described in U.S. Pat. No. 7,077,328, which is incorporated herein by reference in its entirety. As shown, analyte meter 2301 includes a display panel 2302 for displaying instructions and/or results from an analyte measurement, and a user interface 2303 for inputting commands to the analyte meter. Analyte meter 2301 also includes internal processing units (not shown) for the analysis of a blood sample. As such, analyte meter 2301 includes means for analyzing an electrical signal received from an analyte strip port. Analyte meter 2301, however, has been modified to lack a fully integrated analyte test strip port. Instead, analyte meter 2301 provides an electrical interface including electrical contacts corresponding to the electrical contacts of a typical analyte test strip port. Such electrical interface couples with the exposed contact pads 1822 of the electrical interface on the replaceable strip port module 1800 to complete analyte measurement system 2300.

For example, as shown in FIG. 6, analyte meter 2301 includes a receptacle 2310 that provides an opening in the analyte meter housing. Replaceable strip port module 1800 is designed to fit within receptacle 2310. Guide features 2311 are provided in the meter housing to aide in the insertion and alignment of replaceable strip port module 1800 within receptacle 2310. Analyte meter 2301 also includes a screw hole 2313, which aligns with screw hole 2013 in replaceable strip port module 1800. As such, replaceable strip port module 1800 can be removably attached to analyte meter 2301 with a screw 2813 (see FIG. 7). Alternative attachment means may also be employed to removably (or semi-permanently) attach replaceable strip port module 1800 to analyte meter 2301. Screw holes 2013 and 2313, and screw 2813, as well as equivalent structures, thereby serve as means for removably attaching the replaceable strip port module to the analyte meter. In one embodiment, for example, the meter housing and internal components is formed of medical grade PC/ABS plastic blend, and may include an anti-microbial plastic such as BAYER BAYBLEND AM120FR. In one embodiment, meter housing is formed of two or more separate components, which are screwed together using M3 stainless steel screws. Such screws may have heads that differentiate them from the strip port retaining screws. For example, such screws may have Torx heads. Internal screws may be M2.5 zinc-plated, pan head Philips screws.

In operation, contact pads 1822 couple to corresponding open electrical connections (not shown) inside of analyte meter 2301. In one embodiment, the open electrical connections are SIM connections that are electrically coupled to a PCB within analyte meter 2301. In one embodiment, any or all contact pads 1822 or connectors include gold or gold-plating. As such, electrical communication can be provided between analyte test strip port 2000 and analyte meter 2301. In alternative embodiments, the connection between replaceable strip port module 1800 and analyte meter 2301 may be in the form of edge connectors, pin headers, compression connectors, or other equivalent connectors. Such connector forms, and structure equivalent thereto, serve as part of an electrical interface or means for electrically coupling the analyte test strip port to the analyte meter. Additional details regarding various connector forms may be found in U.S. Provisional Patent Application No. 61/406,860 entitled "Modular Analyte Measurement System", filed on Oct. 26, 2010; U.S. patent application Ser. No. 12/175,279, filed on Jul. 17, 2008; the disclosures of which are each incorporated by reference herein in their entirety.

A common analyte strip port requires three functional leads for connection with a meter. In the embodiment shown in FIGS. 4-7, analyte test strip port 2000 provides a line-for-line connection with three of the twelve contact pads 1822. The additional nine contact pads of replaceable strip port module 1800 allow for customization of system 2300. For example, some contact pads may be configured as identification leads to provide various indications to the analyte meter, such as an indication that the replaceable strip port module is connected to the meter, an indication of a type of replaceable strip port module that is connected, and an analyte to be measured. Such customization adds to the functionality of system 2300.

As previously stated above, the replaceable strip port module and analyte meter include electrical interfaces that removably and electrically couple with each other to enable electrical communication between the replaceable strip port module and meter. The following section provides additional detail regarding the electrical interfaces of the analyte meter and replaceable strip port modules.

Electrical Interfaces

Figure 8:
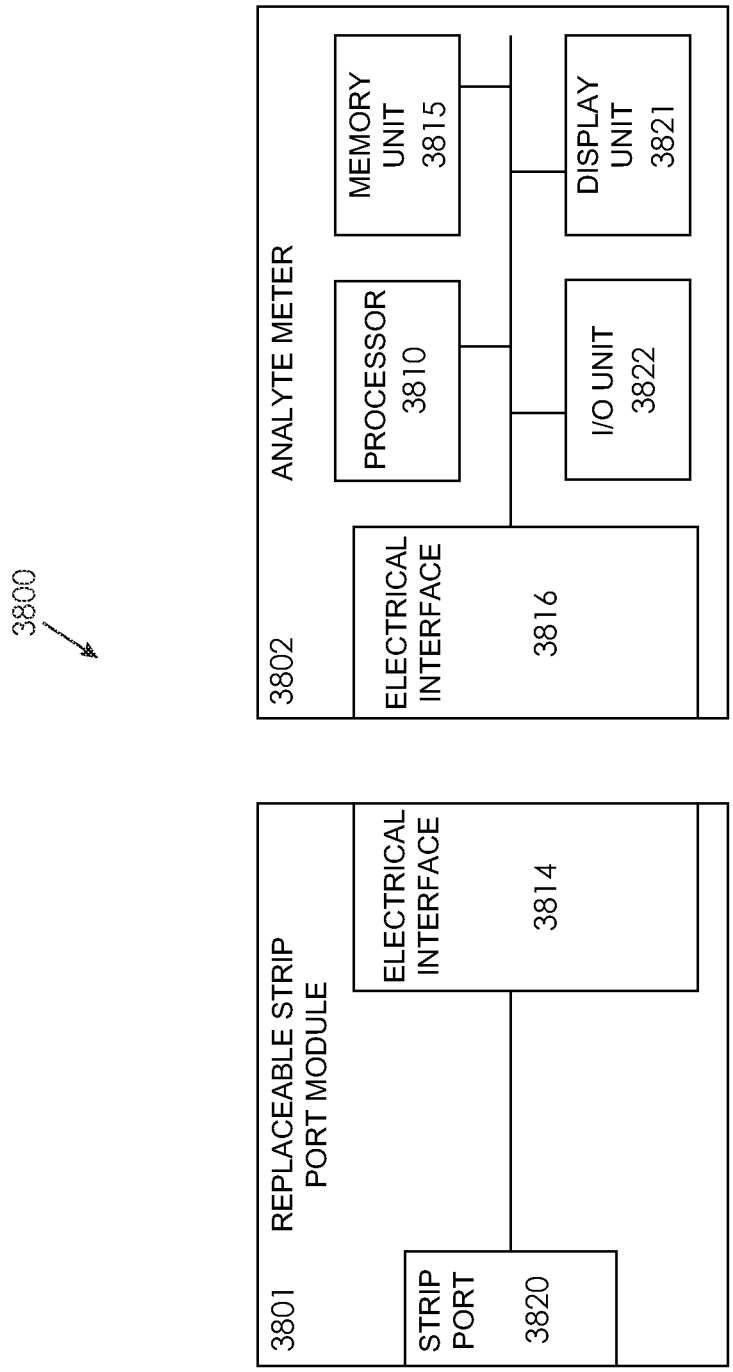
FIG. 8 illustrates a functional block diagram of an analyte measurement system, according to certain embodiments.

FIG. 8 illustrates a functional block diagram of an analyte measurement system, according to certain embodiments. As shown in the example, analyte measurement system 3800 includes replaceable strip port module 3801 that releasably connects and operably couples with an analyte meter 3802. Replaceable strip port module 3801 is shown comprising a strip port 3820 and electrical interface 3814. Strip port 3820 is electrically coupled to electrical interface 3814 and receives an analyte test strip for test measurement. Electrical interface 3814 removably and electrically couples with electrical interface 3816 of analyte meter 3802 when the meter 3802 and replaceable strip port module 3801 are connected, thus providing an electrical path between the strip port 3820 and the analyte meter 3802. Electrical interface 3814 may include various electrical components, such as electrical contacts, signal lines, connectors, and other related electronic circuitry (e.g., biasing circuitry, electrostatic protection circuitry, etc.).

Analyte meter 3802 is shown comprising a processor 3810 that is electrically coupled with electrical interface 3816, memory unit 3815, display unit 3821, and input/output unit 3822. Display unit 3821 may include, for example, hardware components configured to display information to a user at the control of processor 3810. The display unit 421 may be, for example, implemented with a Liquid Crystal Display (LCD), but is not limited thereto. In some embodiments, the analyte meter may not include a display unit 3821, but rather include another form of output such as audible output. Input/output unit 3822 may include for example any variety of input elements for user entry—e.g., buttons, dials, switches, etc. In some instances, the display unit 3822 may be implemented with touchscreen capabilities, in which case the display unit 3822 would also serve as an input element. It should be appreciated that additional components not shown may also be included on the analyte meter 3802 and replaceable strip port module 3801. For example, in some embodiments, the analyte meter 3802 may also include a communication unit that is used to communicate with a remote device via a wired or wireless technology.

Processor 3810 is configured to, for example, control internal timing, perform various algorithms, perform measurement calculations, and to communicate with and control other hardware components, such as display unit 3821, input/output unit 3822, strip port 3820, etc. The term "processor" is used broadly herein and may include any type of processing device or circuitry—e.g., a microprocessor and/or microcontroller. For example, processor 3810 may comprise the MSP430-SD16A microcontroller with analog to digital (A/D) converter from Texas Instruments.

Memory unit 3815 refers broadly to any variety of memory (e.g., volatile and non-volatile), and may include one or more memory components. Memory unit 3815 is electrically coupled to processor 3810 and may store firmware necessary for operation of the analyte meter, as well as various programs that are to be executed by the processor 3810. Furthermore, memory unit 3815 may also store, for example, various data such as, measurement readings, custom settings, user profiles, input entries from users (e.g., food intake, insulin dosage and times, etc.), etc.

Electrical interface 3816 removably and electrically couples with electrical interface 3814 of replaceable strip port module 3801 when the meter 3802 is connected with the replaceable strip port module 3801. In this way, processor 3810 is in electrical communication with strip port 3820 via electrical interface 3814 and 3816, and thus may receive measurement data and various indications from the strip port module 3801. The strip port module may, for instance, indicate to the analyte meter whether the strip port module 3801 is engaged with the analyte meter, what type of replaceable strip port module is connected to the meter, and what type of analyte is to be measured.

Figure 9:
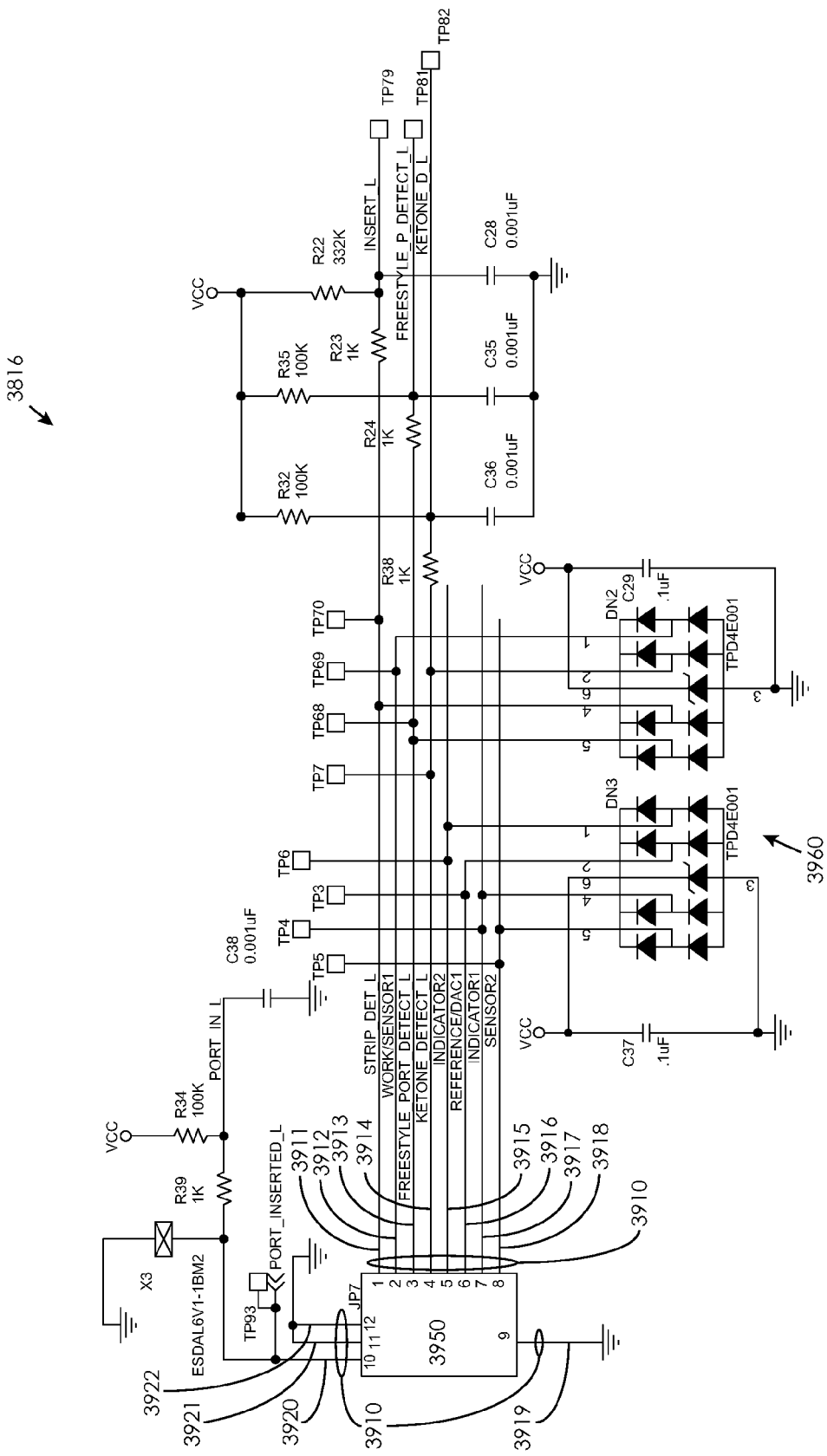
FIG. 9 illustrates a schematic of an electrical interface on an analyte meter, according to certain embodiments.

FIG. 9 illustrates a schematic of an electrical interface on an analyte meter, according to certain embodiments. The electrical interface 3816 is shown comprising various signal lines 3910, connector 3950, and various other circuit elements, such as electrostatic protection circuitry 3960. The electrical interface may be implemented, for example on a printed circuit board (PCB) and coupled to the housing of the analyte meter 3902.

Connector 3950 includes electrical contact pins that removably and electrically couple to the electrical interface 3814 on a replaceable strip port module 3801 when the replaceable strip port module 3801 is connected with the analyte meter 3802. In the embodiment show, connector 3950 includes electrical contact pins 1-12 that are connected to signal lines 3911-3922, respectively. Signal lines 3911-3922 are also referred to collectively as signal lines 3910. Electrical contact pins 9, 11, and 12 of connector 3950 are connected to signal lines 3919, 3921, and 3922, respectively, and are grounded and provide signal ground to corresponding contact pins on replaceable strip port module 3801. Electrical contact pins 1-8 and 10 of connector 3950 are connected to signal lines 3911-3918 and 3920, respectively, and electrically couple to corresponding contact pins on the replaceable strip port module when coupled.

The term "signal line" is used herein to refer generally to electrically conductive lines such as traces on a printed circuit board (PCB) that enable the transfer of electrical signals. The term "signal" is used herein to refer generally to any type of electrical signal that may be provided on the signal line—e.g., analog signal or digital signal, including logic low level signals (e.g., signal ground) and logic high level signals.

Some signal lines of signal lines 3910 are shown electrically coupled to ground, while the others are electrically coupled to processor 3810 and are used to provide signals to and/or from processor 3810. For example, for the embodiment shown, signal lines 3910 include a port insertion signal line 3920 connected to pin 10 of connector 3950, which carries a port insertion signal that indicates to processor 3810 when a replaceable strip port module 3801 is coupled to the meter 3902. Signal lines 3910 also include port-type signal line 3913 connected to pin 3, which is used to indicate to processor 3810 what type of replaceable strip port module is coupled to the analyte meter 3902. Signal lines 3910 also include an analyte-type signal lines 3911 and 3914 connected to pins 1 and 4 of connector 3950, respectively, which carry analyte type signals that indicate to processor 3810 what type of analyte is to be measured.

Figure 13:
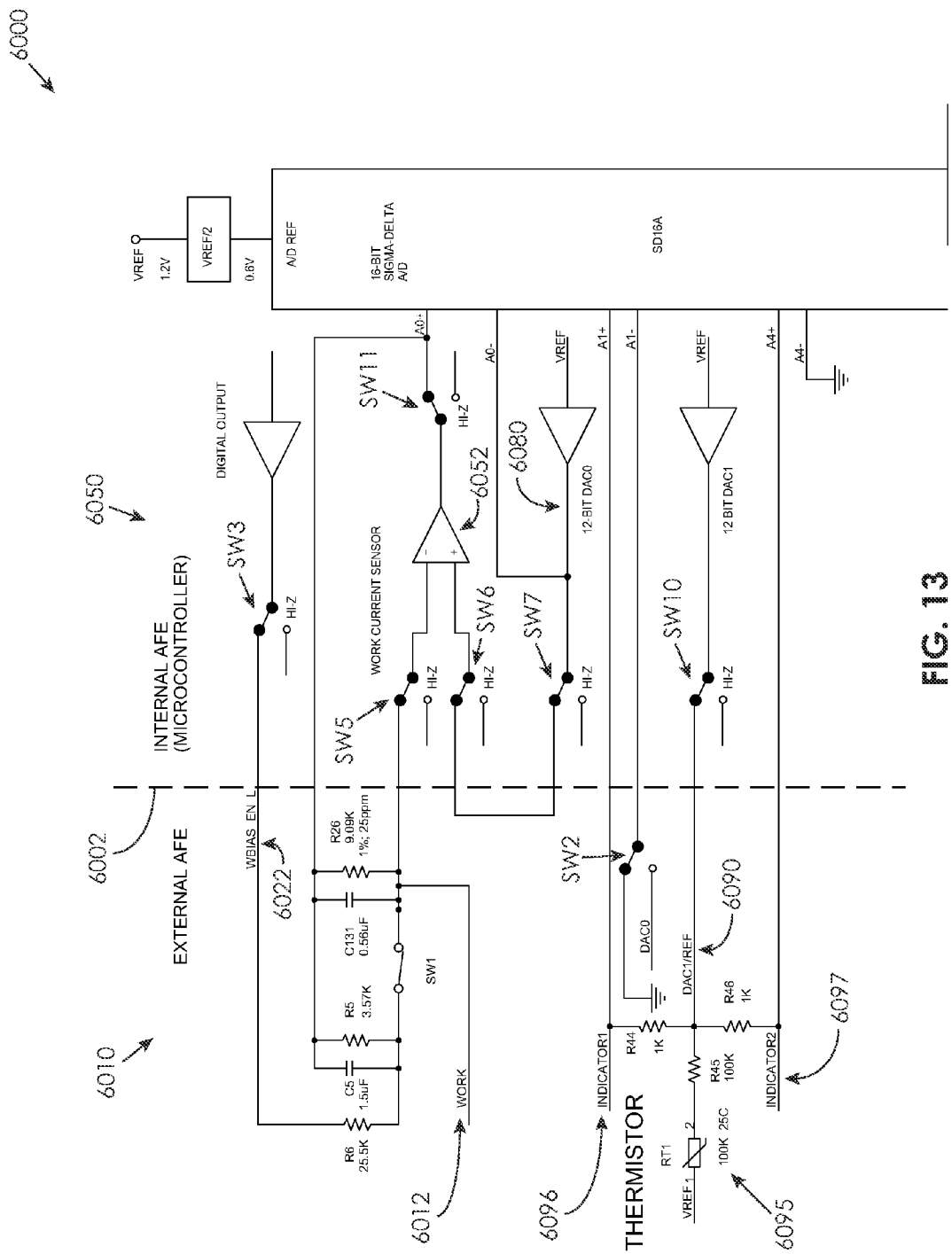
FIG. 13 illustrates an analog front end configuration for a glucose measurement when another example type of replaceable strip port module is connected to the analyte meter, according to some embodiments.

Signal lines 3910 also include various signal lines used for measurement related purposes. For example, signal lines 3912 and 3918 are shown connected to pins 2 and 8 of connector 3850, respectively, and are used to carry signals from the analyte sensor—e.g., current signals from the work and/or trigger electrodes—to the processor 3810. Signal lines 3915 and 3917 are shown connected to pins 5 and 7 of connector 3850, respectively. Signal lines 3915 and 3917 may, for example, be used as additional measurement inputs that can be used for other measurement types. For instance, in some strip port modules, signal lines 3915 and 3917 may be coupled to different blood fill indicator electrodes on a test strip, and carry indicator signals that are used to indicate which blood fill indicator electrode has received a blood sample for measurement. In some instances, a test strip may include two or more blood fill indicator electrodes—e.g., having two places to apply blood, such as one the sides of a test strip for a left-handed user or a right-handed user. For example, some versions of FreeStyle® and FreeStyle Lite® analyte test strips from Abbott Diabetes Care Inc., Alameda, Calif., include more than one blood fill indicator electrodes. In other instances, a test strip may include only one blood fill indicator electrode (e.g., at the back of the test strip), in which case signal lines 3915 and 3917 are not necessary to provide such blood fill indication. For example, some versions of Precision Extra® and Precision XceedPro® analyte test strips from Abbott Diabetes Care Inc., Alameda, Calif., include only a single blood fill indicator electrode. Signal line 3916 is shown connected to pin 6 of connector 3850 and is used to carry a reference signal that, in some embodiments such as shown in FIG. 13, bias the above-described indicator signals and work channel. Signal line 3916 may also be used to provide strip port module 3801 with a DAC output used for instrumentation, and in some instances, for temperature measurement at the strip port. As stated above, pins 9, 11, and 12 of connector 3950 are connected to ground and provide a signal ground to the replaceable strip port module 3801. It should be appreciated that connector 3950, as well as other connectors described herein, and are not limited to connectors having "pins" per se, but may rather include any type of suitable electrical contact. For example, connector 3950 may include electrical contacts in the form of sockets that receive electrical contact pins from the electrical interface of the replaceable strip port module, or vice versa.

In certain embodiments, analyte meter receives an indication that a replaceable strip port module has been connected to the analyte meter. For example, electrical interface 3816 may receive a port insertion signal from a connected replaceable strip port module 3801 and provide the port insertion signal to the processor 3810 (not shown in FIG. 9) via the port insertion signal line 3920. The port insertion signal is used to indicate to the processor 3810 that a replaceable strip port module 3801 is coupled to the analyte meter 3802. For example, for the active-low port insertion signal line 3920 shown in FIG. 9, a logic low signal indicates that a replaceable strip port module 3801 is coupled, while a logic high signal indicates that a replaceable strip port module 3801 is not coupled.

Port insertion signal line 3920 is connected to pin 10 of connector 3850, which electrically couples with a corresponding electrical contact on the replaceable strip port module 3801 when coupled. In this way, the replaceable strip port module 3801 may provide the appropriate signal to the analyte meter 3802 to indicate that the strip port module 3801 is coupled to the analyte meter 3802. For instance, if port insertion signal line 3920 is held high when a replaceable strip port module 3801 is not coupled to the analyte meter 3802, then the replaceable strip port module 3801 may provide a logic low signal (e.g., ground signal) to pin 10 of connector 3850 when the two are coupled. Port insertion signal line 3920 is pulled low and the logic low signal is transmitted to the processor 3810 which initiates the appropriate actions accordingly. For example, the processor may then determine what type of replaceable strip port module is connected, what analyte to measure, etc., and configure the analyte meter for proper operation with the connected replaceable strip port module. The above-described configuration, and equivalents thereof, serve as means for receiving a port insertion signal when a replaceable strip port is connected and for providing the port insertion signal to the processor. It should be appreciated that in other embodiments other signaling schemes may be implemented and/or more than one signal line may be implemented for a particular signal (e.g., the port-insertion signal).

In some aspects, the analyte meter releasably connects and operably couples with different types of replaceable strip port modules. The term "type", as used in relation to the type of replaceable strip port module, is used herein to refer to different form factors and/or different testing techniques implemented in the replaceable strip port modules. In other words, different types of replaceable strip port modules may have different form factors and/or testing techniques from one another. The "form factor" of the replaceable strip port module refers to the test strip interface configuration of the strip port. For example, electrical contacts on the strip ports may have different sizes, shapes, orientations, placement locations, etc., for compatibility with analyte test strips having different form factors. The form factor of the test strip may include, for example, the size and shape of the test strip, as well as the electrical contact configuration of the test strip. For example, one type of replaceable strip port module may have a form factor that includes a strip port having electrical contacts properly positioned to couple with an analyte test strip having electrical contacts on the top and bottom of the analyte test strip. Another type of replaceable strip port module may have a form factor that, for example, includes a strip port having electrical contacts properly positioned to couple with an analyte test strip having electrical contacts only on the top of the test strip. Testing techniques implemented in replaceable strip port modules may include, for example, coulometry, amperometry, or any other suitable technique for determining a concentration of analyte.

Examples of suitable analyte test strips having opposing or co-planar electrode configurations are depicted in FIGS. 15A-15E. As shown in FIG. 15A, an analyte test strip 8200 has an opposing electrode configuration with electrode contact 8201 positioned on a first substrate 8205, electrode contacts 8202, 8203 and 8204 positioned on a second substrate 8206, wherein the first and second substrates are separated by a spacer (not shown). Turn-on contacts 8400 is configured to contact corresponding turn-on contacts on the meter to facilitate certain functions of the analyte meter—e.g., to facilitate detection of an analyte test strip by the analyte meter upon insertion of the test strip into the strip port. In one embodiment, such detection results in activation of the analyte meter for testing in the absence of further action by the user such as manipulation of a switch on the analyte meter. Additional embodiments of analyte test strips 8200 are shown in FIG. 15B and FIG. 15D. Analyte test strips of this form factor include analyte test strips available from Abbott Diabetes Care Inc., Alameda, Calif., e.g., FreeStyle® and FreeStyle Lite® glucose monitoring test strips. As shown in FIGS. 15C and 15E, analyte test strip 8300 have a co-planar electrode configuration with electrode contacts 8301, 8302 and 8303 positioned on a substrate 8304. Analyte sensors of this form factor include analyte test strips available from Abbott Diabetes Care Inc., Alameda, Calif., e.g., Precision Extra® and Precision XceedPro® glucose and ketone monitoring test strips. In certain embodiments, one type of replaceable strip port module includes a form factor and testing technique compatible with FreeStyle® and FreeStyle Lite® analyte test strips from Abbott Diabetes Care Inc., Alameda, Calif., and another type of replaceable strip port module includes a form factor and testing technique compatible with Precision Extra® and Precision XceedPro® analyte test strips from Abbott Diabetes Care Inc., Alameda, Calif. Additional details regarding form factors and testing techniques for analyte test strip ports may be found in U.S. patent application Ser. No. 12/695,947 entitled "Universal Test Strip Port", filed on Jan. 28, 2010; U.S. Pat. No. 6,773,671 entitled "Multichemistry Measuring Device and Test Strips", filed on Nov. 17, 1999; the disclosures of which are each incorporated by reference herein in its entirety.

Because an analyte meter may be connected to different types of replaceable strip port modules, the analyte meter may need to configure itself for proper operation with the specific type of replaceable strip port module connected. For example, the analyte meter may configure its analog front end electronics for proper operation with the specific type of replaceable strip port module that is connected. The replaceable strip port module may, for example, indicate to the analyte meter what type of replaceable strip module it is so that the analyte meter may be configured accordingly and the proper analyte measurement algorithm implemented. For example, in one embodiment, the device software is designed to support multiple types of analyte measurement algorithms and when a certain type of replaceable strip port module is inserted into the analyte monitoring device, the device software detects which type of strip port is being used, loads the matching algorithm software, and configures the analog front end accordingly so that the analyte data sampling and calculation are performed correctly for the corresponding strip type. It should be appreciated that some replaceable analyte strip ports may be configured to operate with analyte test strips that measure a specific analyte (e.g., glucose and/or ketone bodies), and that in some embodiments, the detection of the type of replaceable strip port module may encompass the identification of the type of analyte to test for. In such case, when the device software detects which type of strip port is being used and consequently what type of analyte is to be measures, the device software loads the matching algorithm software, and configures the analog front end accordingly so that the analyte data sampling and calculation are performed correctly for the corresponding strip type and analyte.

Figure 10A:
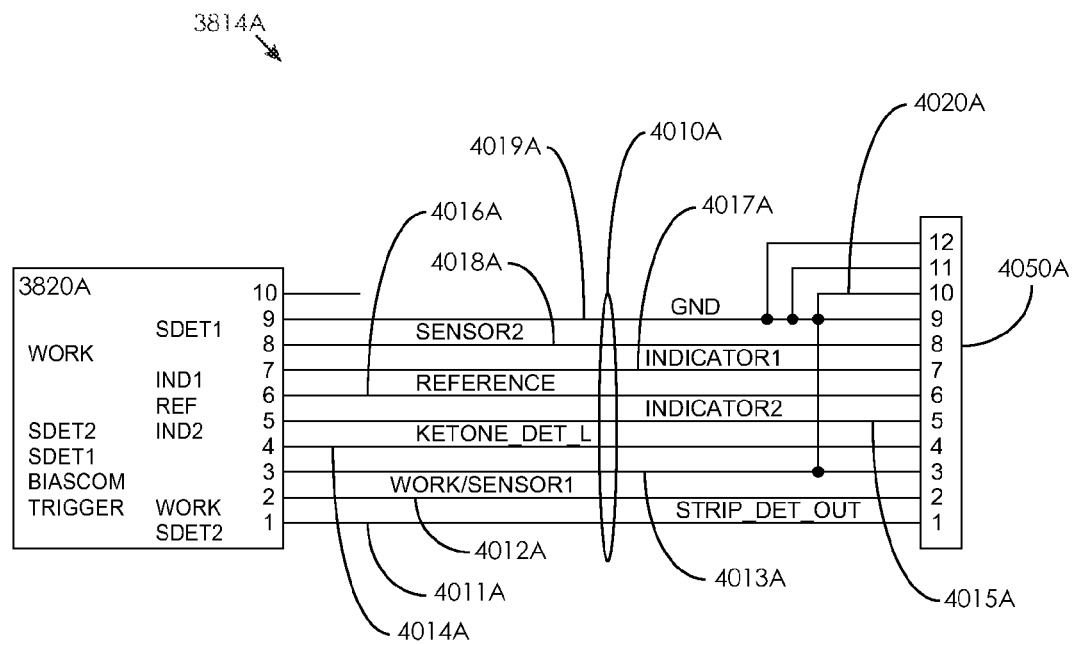
FIG. 10A illustrates an electrical interface for a first type of replaceable strip port module, according to certain embodiments.
Figure 10B:
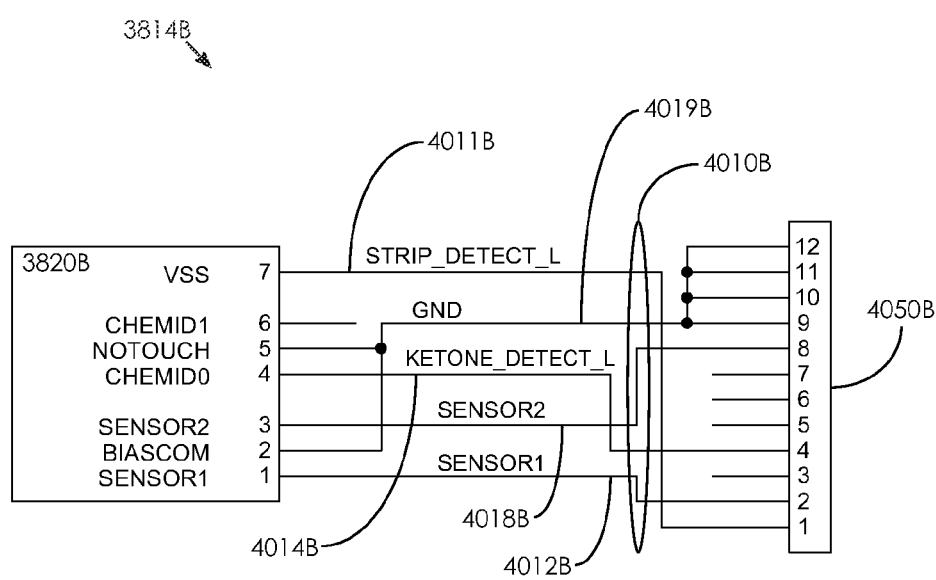
FIG. 10B illustrates an electrical interface for a second type of replaceable strip port module, according to certain embodiments.

In certain embodiments, the analyte meter 3802 receives an indication of the type of replaceable strip port module 3801 that is connected. For example, the electrical interface 3816 may receive a port-type signal to indicate a first type of replaceable strip port module 3801 has been coupled to the analyte meter 3802. In FIG. 9, for instance, electrical interface 3816 is shown including an active-low port-type signal line 3913 that is used to indicate to the processor 3810 (not shown in FIG. 9) what type of replaceable strip port module is connected to the meter 3802. Port-type signal line 3913 is electrically coupled to processor 3810 and also to pin 3 of connector 3850, which electrically engages a corresponding electrical contact on a replaceable strip port module when coupled. A first type of replaceable strip port module may, for example, provide a logic low signal to pin 3 of connector 3850 when connected, which indicates to meter 3802 that a first type of replaceable strip port module 3801 is connected. FIG. 10A, discussed in further detail later, illustrates such an example first type of replaceable strip port module. On the other hand, a second type of replaceable strip port module may, for example, maintain a logic high signal on the port-type signal line 3913, which indicates that a second type of replaceable strip port module 3801 is coupled to the analyte meter 3802. For example, the second type of replaceable strip port module may include a floating pin that connects with pin 3 of connector 3850 to maintain the current signal carried on port-type signal line 3913. FIG. 10B, discussed in further detail later, illustrates such an example second type of replaceable strip port module.

Depending on specific type of replaceable strip port module indicated, processor 3810 thereafter initiates the appropriate actions to operate properly with that type of replaceable strip port module 3801. The above-described configurations, and equivalents thereof, serve as means for receiving an indication of what type of replaceable strip port module is connected and for providing the indication to the processor. It should be appreciated that in other embodiments other signaling schemes may be implemented and/or more than one signal line may be implemented for one signal. For example, two signal lines may be implemented to provide signals for up to four different types of replaceable strip port modules; three signal lines to provide signals for up to eight different types of replaceable strip port modules, etc.

In some aspects of the present disclosure, the analyte meter receives an indication as to the type of analyte to be measured. In some instances, one type of replaceable strip port module is capable of receiving analyte test strips for different analyte measurements. For example, one type of replaceable strip port module may be capable of receiving glucose and ketone test strips with compatible form factors as the form factor of the replaceable strip port module. Other suitable analytes may also be applicable.

In some aspects, the analyte meter receives an indication of the type of analyte to be measured. For instance, when a test strip for a specific analyte is inserted into the strip port of a connected replaceable strip port module 3801, the type of analyte to be measured is indicated to the analyte meter 3802 by the replaceable strip port module 3801 so that the meter 3802 may operate properly for the appropriate analyte to be measured—e.g., to obtain the appropriate readings, to perform the appropriate calculations, etc. Upon connection to the analyte meter, for example, the replaceable strip port module may indicate to the analyte meter what type of analyte is to be measured so that the analyte meter may be configured accordingly and the proper analyte measurement algorithm implemented. For example, some analyte strip ports are configured to be used analyte test strips for a specific analyte (e.g., glucose and/or ketone bodies). In one embodiment, the device software is designed to support multiple types of analyte measurement algorithms (e.g., multiple types of glucose and ketone measurement algorithms). When a certain type of replaceable strip port module is inserted that measures a specific analyte (e.g., glucose and/or ketone bodies), the device software detects which type of analyte is to be measured, loads the matching algorithm software, and configures the analog front end accordingly so that the analyte data sampling and calculation are performed correctly for the corresponding analyte.

For example, in some embodiments, the electrical interface 3816 receives an analyte-type signal that indicates what type of analyte is to be measured. Test strips may include, for example, indicators that indicate what type of analyte is applicable for that test strip. The test strip may be configured to electrically connect various electrical contacts on the strip port 3820 depending on what analyte-specific test strip (e.g., glucose or ketone test strip) is inserted. The indicator may be implemented as electrical contacts that electrically couple two or more pins on the strip port. For example, the indicator may electrically couple a grounded pin on the strip port with the pin on the strip port that is electrically coupled to analyte-type signal line, thus pulling the analyte-type signal line low to indicate to processor 3810 the specific analyte to be measured. Additional details regarding different analyte test strips and various indicator configurations thereon, may be found in U.S. Pat. No. 6,773,671 entitled "Multichemistry Measuring Device and Test Strips", filed on Nov. 17, 1999; the disclosure of which is incorporated by reference herein in its entirety.

For example, in certain embodiments, the replaceable strip port module 3801 receives a test strip and provides the appropriate analyte-type signal to the electrical interface 3816 based on the test strip and its indicator. For example, the test strip may include an electrical contact configuration that electrically couples two or more pins of the strip port 3820 to provide a ground signal to the appropriate contact pin on electrical interface 3814 that is electrically coupled with the corresponding analyte-type signal line 3911 or 3914 on the electrical interface 3816 of the analyte meter 3802.

In certain embodiments, such as the one shown in FIG. 9, electrical interface 3816 includes two analyte-type signal lines 3911 and 3914 that carry analyte-type signals to processor 3810. For example, an analyte-type signal carried on analyte-type signal line 3911 indicates that a first analyte-specific test strip (e.g., a glucose test strip) is inserted into the strip port module 3820, while an analyte-type signal on analyte-type signal line 3914 indicates that a second analyte-specific test strip (e.g., ketone test strip) is inserted into the strip port 3820. In FIG. 9, analyte-type signal lines 3911 and 3914 are shown as active-low signal lines. Thus, a logic low level signal on analyte-type signal line 3911 indicates that a glucose measurement is required—e.g., that a glucose test strip has been inserted into the strip port 3820. Similarly, a logic low level signal on analyte-type signal line 3914 indicates that a ketone measurement is required—e.g., that a ketone test strip has been inserted into strip port 3820. It should be appreciated that in other embodiments, other signaling schemes may be implemented and/or a different number of signal lines implemented—e.g., a single signal line and two logic levels may be implemented to indicate two different analyte measurements, as similarly described above for the port-type signal line.

Analyte-type signal line 3911 and 3914 are coupled to pin 1 and 4 of connector 3950, respectively, which electrically connect with corresponding electrical contacts on replaceable strip port module 3801 when coupled. In this way, depending on which analyte-specific test strip is inserted into the strip port 3820, the replaceable strip port module 3801 provides the appropriate analyte-type signal to the analyte meter 3802 to indicate what type of analyte is to be measured. When a specific analyte-type signal is received by the processor 3810, the processor initiates the appropriate actions to operate properly for that specific analyte measurement. The above-described configurations, and equivalents thereof, serve as means for receiving an analyte-type signal and for providing the analyte-type signal to the processor.

As stated above, the replaceable strip port module also provides various measurement related signals to the analyte meter—e.g., signals from sensor electrodes such as trigger and/or work electrodes—and may further provide an indication as to whether a replaceable strip port module is connected, what type of strip port module is connected, what type of analyte is to be measured, etc. When the replaceable strip port module 3801 is connected to the analyte meter 3802, the electrical interface 3814 is electrically coupled to electrical interface 3816 to provide an electrical path between the two devices.

FIGS. 10A and 10B illustrate schematics for different electrical interfaces on for different types of replaceable strip port modules, according to certain embodiments. FIG. 10A illustrates an electrical interface for a first type of replaceable strip port module (e.g., strip port module having a first form factor and testing technique). FIG. 10B illustrates an electrical interface for a second type of replaceable strip port module (e.g., strip port module having a second form factor and testing technique).

In FIG. 10A, electrical interface 3814A is shown comprising connector 4050A, strip port 3820A, and signal lines 4010A. Connector 4050A includes twelve electrical contact pins 1-12 that removably and electrically couple with the same numbered electrical contact pin on connector 3950—e.g., pin 1 of connector 4050A is connected to pin 1 of connector 3950; pin 2 of connector 4050A is connected to pin 2 of connector 3950; pin 3 of connector 4050A is connected to pin 3 of connector 3950; etc. Strip port 3820A includes the appropriate form factor to receive and operably couple with an analyte test strip having a compatible form factor. Strip port 3820A includes electrical contact pins 1-10. Signal lines 4010A connect connector 4050A with strip port 3820A.

Pin 9 of strip port 3820A is connected to grounded pin 9 of connector 4050A via signal line 4019A. Pin 9 of connector 4050A is grounded because it connects with grounded pin 9 of connector 3950. Electrical interface 3814A is shown connecting pin 10 of connector 4050A to grounded pin 9 of connector 4050A, thus providing a ground signal to port-insertion signal line 3920 to indicate that a replaceable strip port module is connected.

Pin 3 of strip port 3820A is connected to pin 3 of connector 4050A by signal line 4013A, and is further grounded by a connection to grounded pin 9 of strip port 3820A, thus providing a ground signal to port-type signal line 3913 to indicate that a first type of replaceable strip port module 3801 is connected to the meter 3802.

Pins 1 and 4 of strip port 3820A are connected to pins 1 and 4 of connector 4050A by signal lines 4011A and 4014A, respectively. Depending on whether the test strip is designed for a glucose or ketone measurement, the indicator on the test strip electrically couples grounded pin 9 of strip port 3820A to either pin 1 or pin 4 of strip port 3820A, thus providing a ground signal to the appropriate analyte-type signal line 3911 or 3914 on the electrical interface 3816. It should be appreciated that in some instances the indicator may couple either pin 7 or pin 4 of strip port 3820B to another pin on strip port 3820B that is held low, thus achieving achieving the low level signal on the appropriate analyte-type signal line 3911 or 3914.

Pins 2 and 8 of strip port 3820A are connected to pins 2 and 8 of connector 4050A by signal lines 4012A and 4018A, respectively. The current signal from the analyte test strip (e.g., from the work or trigger electrode) may be provided via pins 2 and 8 of strip port 3820A to the corresponding sensor signal lines 3912 or 3918 on electrical interface 3816, respectively.

Pins 6 of strip port 3820A is connected to pin 6 of connector 4050A by signal line 4016A, thus providing electrical connection for the reference signal on reference line 3916. Pins 5 and 7 of strip port 3820A are connected to pins 5 and 7 of connector 4050A by signal lines 4015A and 4017A, respectively, thus providing electrical connection for the indicator signals on the indicator signal lines 3917 and 3915.

The strip port 3820A shown in FIG. 10A receives and operates with one or more analyte-specific test strips having the same form factor. For example, in one embodiment, strip port 3820B operates with FreeStyle® and FreeStyle Lite® analyte test strips from Abbott Diabetes Care Inc., Alameda, Calif. As stated before, the replaceable strip port module 3801 indicates various information to the analyte meter 3802 to operate properly with the specific strip port module 3801 connected therewith—e.g., whether a strip port module is connected, what type of strip port module is connected, and what type of analyte is to be measured. Furthermore, the replaceable strip port module 3801 communicates various measurement related signals—e.g., signals from electrodes such as trigger and/or work electrodes—to the analyte meter 3802.

In certain embodiments, electrical interface 3814A indicates to the analyte meter 3802 when the strip port module 3801 is connected. In a preferred embodiment, the indication is provided to the analyte meter upon connection and without user entry to indicate that the replaceable strip port module is connected. For example, pin 10 of connector 4050A is tied to pins 9, 11, and 12 of connector 4050A, which are electrically coupled with grounded pins 9, 11, and 12 of connector 3950. Therefore, pin 10 of connector 4050A provides a logic low signal to active-low port insertion signal line 3920 of electrical interface 3816 when the strip port module 3801 is coupled to the meter 3802, thus indicating that a replaceable strip port module is connected. The above-described configurations, and equivalents thereof, serve as means for indicating to the analyte meter when the replaceable strip port module is connected.

In certain embodiments, electrical interface 3814A indicates to the analyte meter 3802 what type of strip port module 3801 is connected with the meter 3802. In a preferred embodiment, the indication is provided to the analyte meter upon connection and without user entry to indicate what type of replaceable strip port module is connected. Pin 3 of connector 4050A is tied to pins 9, 11, and 12 of connector 4050A which are grounded by pins 9, 11, and 12 of connector 3950. Therefore, pin 3 of connector 4050A provides a logic low signal on the port-type signal line 3913 of electrical interface 3816 when the strip port module 3801 is coupled to the meter 3802, thus indicating that a first type of strip port module is connected to the meter 3802. The above-described configurations, and equivalents thereof, serve as means for indicating to the analyte meter what type of strip port module is connected with the meter.

In certain embodiments, electrical interface 3814A indicates to the analyte meter what type of analyte is to be measured—e.g., after a test strip is inserted into strip port 3820A. In a preferred embodiment, the indication is provided to the analyte meter upon insertion of a test strip into the strip port and without user entry to indicate that the analyte to be measured. Analyte-type signal line 4011A connects pin 1 of strip port 3820A with pin 1 of connector 4050A, which removably and electrically couples to pin 1 of connector 3950 and analyte-type signal line 3911 of electrical interface 3816 described above. Similarly, analyte-type signal line 4014A connects pin 4 of strip port 3820A with pin 4 of connector 4050A, which removably and electrically couples to pin 4 of connector 3950 and analyte-type signal line 3914 of electrical interface 3816 described above.

For example, in the embodiment shown, when a glucose test strip is inserted into strip port 3820A, the glucose test strip provides a logic low signal to the signal line 4011A—e.g., by electrically connecting pin 1 of strip port 3820A to grounded pin 9 of strip port 3820A. On the other hand, when a ketone test strip is inserted into strip port 3820, the ketone test strip provides a logic low signal to signal line 4014A—e.g., by electrically connecting pin 4 of strip port 3820A to grounded pin 9 of strip port 3820A. It should be appreciated that the indicator may couple any other pin of strip port 3820B that is held low to either pin 7 or pin 4 of strip port 3820B to achieve the low level signal on the appropriate analyte-type signal line 3911 or 3914. For example, processor 3810 may hold indicator signal line 3915 low, which keeps indicator signal line 4015A and pin 5 of strip port 3820A low. Therefore, electrically connecting either pin 7 or pin 4 of strip port 3820A to pin 5 of strip port 3820A would pull the appropriate analyte-type signal line 3911 or 3914 low. The above-described configurations, and equivalents thereof, serve as means for indicating to the analyte meter what type of analyte is to be measured.

Electrical interface 3814A also carries various measurement related signals. Reference signal line 4016A connects pin 6 of strip port 3820A to pin 6 of connector 4050A, which removably and electrically couples to reference signal line 3916 of electrical interface 3816 described above. Further, sensor signal line 4012A connects pin 2 of strip port 3820A with pin 2 of connector 4050A, which removably and electrically couples to sensor signal line 3912 of electrical interface 3816 as described above. Signal line 4018A connects pin 8 of strip port 3820A with pin 8 of connector 4050A, which removably and electrically couples to sensor signal line 3918 of electrical interface 3816 as described above. For example, current signals from the trigger and/or work electrodes may be transmitted from the strip port 3820A to the analyte meter 3802 via the sensor signal lines 4012A and 4018A. Furthermore, indicator line 4015A connects pin 5 of strip port 3820A with pin 5 of connector 4050A, which removably and electrically couples to pin 5 of connector 3950 and indicator signal line 3915 of electrical interface 3816 described above. Indicator line 4017A connects pin 7 of strip port 3820A with pin 7 of connector 4050A, which removably and electrically couples to pin 7 of connector 3950 and indicator signal line 3917 of electrical interface 3816 described above.

As stated above, FIG. 10B illustrates an electrical interface for a second type of replaceable strip port module (e.g., strip port module having a second form factor and testing technique). In FIG. 10B, electrical interface 3814B is shown comprising connector 4050B, strip port 3820B, and signal lines 4010B. Connector 4050B includes twelve electrical contact pins 1-12 that removably and electrically couple with the same numbered electrical contact pin on connector 3950—e.g., pin 1 of connector 4050B is connected to pin 1 of connector 3950; pin 2 of connector 4050B is connected to pin 2 of connector 3950; pin 3 of connector 4050B is connected to pin 3 of connector 3950; etc. Strip port 3820B is shown having seven electrical contact pins 1-7.

Pins 2 and 5 of strip port 3820B are connected to grounded pin 9 of connector 4050B. Electrical interface 3814B is shown connecting pin 10 of connector 4050A to grounded pin 9 of connector 4050B, thus providing a ground signal to port-insertion signal line 3920 to indicate that a replaceable strip port module is connected.

Electrical interface 3914B comprises floating pin 3 of connector 4050B. Therefore, a ground signal is not provided to signal line 3913 of electrical interface 3916, thus maintaining the existing signal on signal line 3913 to indicate that a second type of replaceable strip port module is connected to the meter. Furthermore, electrical interface 3914B comprises floating pin 5, 6, and 7, therefore the indicator signal lines 3915 and 3917 and reference signal line 3916 are not electrically coupled to the strip port 3820B.

Pins 7 and 4 of strip port 3820B are connected to pins 1 and 4 of connector 4050B by signal lines 4011B and 4014B, respectively. Depending on whether the test strip is designed for a glucose or ketone measurement, an indicator on the test strip electrically couples a grounded pin (e.g., pin 2 or 5) of strip port 3820B to either pin 7 or pin 4 of strip port 3820B, thus providing a ground signal to the appropriate analyte-type signal line 3911 or 3914 on the electrical interface 3816. It should be appreciated that the indicator may couple any other pin of strip port 3820B that is held low to either pin 7 or pin 4 of strip port 3820B to achieve the low level signal on the appropriate analyte-type signal line 3911 or 3914.

Pins 1 and 3 of strip port 3820B are connected to pins 2 and 8 of connector 4050A by signal lines 4012BA and 4018B, respectively. The current signal from the analyte sensor (e.g., from the work or trigger electrode) may be provided via pins 2 and 8 to the corresponding sensor signal lines 3912 or 3918 on electrical interface 3816, respectively.

Strip port 3820B receives and operates with one or more analyte-specific test strips having the same form factor as each other, but different from the test strips used with the strip port 3820A shown in FIG. 10A. For example, in one embodiment, strip port 3820B operates with Precision Extra® and Precision XceedPro® analyte test strips from Abbott Diabetes Care Inc., Alameda, Calif. The replaceable strip port module of FIG. 10B also indicates to the analyte meter information such as whether a strip port module is connected, what type of strip port module is connected with the meter, and what type of analyte is to be measured. Furthermore, the replaceable strip port module communicates various measurement related signals—e.g., signals from electrodes such as trigger and/or work electrodes, reference signals, etc.

In certain embodiments, electrical interface 3814B indicates to the analyte meter 3802 when the strip port module 3801 is connected with the meter 3802. For example, pin 10 of connector 4050B is tied to pins 9, 11, and 12 of connector 4050B, which are electrically coupled with grounded pins 9, 11, and 12 of connector 3950. Therefore, pin 10 of connector 4050B provides a logic low signal to active-low port insertion signal line 3920 of electrical interface 3816 when the strip port module 3801 is connected to meter 3802, thus indicating that a replaceable strip port module is connected. The above-described configurations, and equivalents thereof, serve as means for indicating to the analyte meter when the replaceable strip port module is connected.

In certain embodiments, electrical interface 3814B indicates to the analyte meter what type of strip port module 3801 is connected with meter 3802. For example, pin 3 of connector 4050B, which removably and electrically couples to pin P3 of connector 3950 and port-type signal line 3913 of electrical interface 3816, is left floating and thus does not affect the signal on port-type signal line 3913. Therefore, the electrical interface 3814B indicates that a second type of strip port module is connected by maintaining the existing logic high signal on port-type signal line 3913 of electrical interface 3816. Processor 3810 of meter 3802, having already received an indication that a strip port module 3801 has been connected, determines that the strip port module is of a second type because the logic high signal on port-type signal line 3913 of electrical interface 3816 remained the same and did not change when the strip port module 3801 was connected to the meter 3802. The above-described configurations, and equivalents thereof, serve as means for indicating to the analyte meter what type of strip port module is connected with the meter.

In certain embodiments, electrical interface 3814B indicates to the analyte meter what type of analyte is to be measured—e.g., after a test strip is inserted into the strip port 3820B. For example, analyte-type signal line 4011B connects pin 7 of strip port 3820B with pin 1 of connector 4050B, which removably and electrically couples to pin 1 of connector 3950 and analyte-type signal line 3911 of electrical interface 3816 described above. Similarly, analyte-type signal line 4014B connects pin 4 of strip port 3820B with pin 4 of connector 4050B, which removably and electrically couples to pin 4 of connector 3950 and analyte-type signal line 3914 of electrical interface 3816 described above.

For example, in the embodiment shown, when a glucose test strip is inserted into strip port 3820B, the glucose test strip provides a logic low signal to the signal line 4011B—e.g., by electrically connecting pin 7 of strip port 3820A to any pin of strip port 3820B that is held low or grounded, such as pin 2 or 5 of strip port 3820B which is connected to grounded pin 9 of connector 4050B. On the other hand, when a ketone test strip is inserted into strip port 3820, the ketone test strip provides a logic low signal to signal line 4014B—e.g., by electrically connecting pin 4 of strip port 3820B to any pin of strip port 3820B that is held low or grounded, such as pin 2 or 5 of strip port 3820A which is connected to grounded pin 9 of connector 4050B.

Electrical interface 3814B also transmits various measurement related signals. Sensor signal line 4012B connects pin 1 of strip port 3820B with pin 2 of connector 4050B, which removably and electrically couples to pin 2 of connector 3950 and port-type signal line 3912 of electrical interface 3816 described above. Sensor signal line 4018B connects pin 3 of strip port 3820B with pin 8 of connector 4050B, which removably and electrically couples to pin 8 of connector 3950 and port-type signal line 3918 of electrical interface 3816 described above. For example, current signals from the trigger and/or work electrodes may be transmitted from the strip port 3820B to the analyte meter 3802 via the sensor signal lines 4012B and 4018B. Pins 3, 5, 6, and 7 of connector 4050B, which connect with pins 3, 5, 6, and 7 of connector 4050B, respectively, are left floating. The above-described configurations, and equivalents thereof, serve as means for indicating to the analyte meter what type of analyte is to be measured.

Figure 11:
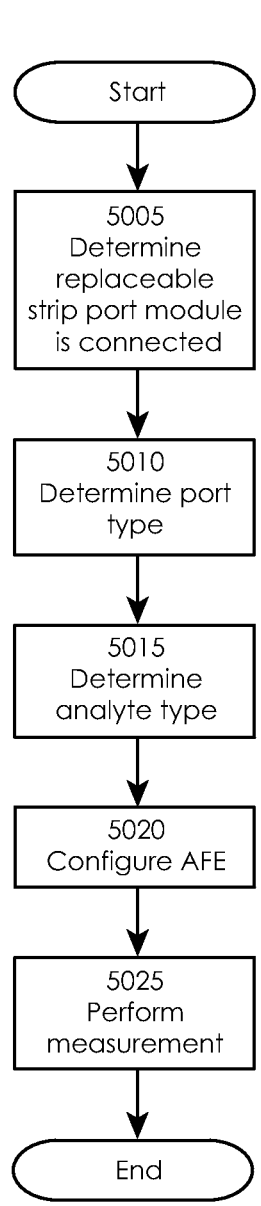
FIG. 11 illustrates a flow chart for configuring an analyte meter for a measurement when a replaceable strip port module is connected to the meter, according to certain embodiments.

FIG. 11 illustrates a flow chart for configuring an analyte meter for a measurement when a replaceable strip port module is connected to the meter, according to certain embodiments. When the replaceable strip port module 3801 is connected to the analyte meter 3802, the replaceable strip port module 3801 provides a port insertion signal to the analyte meter to indicate that the strip port module 3801 is connected. The analyte meter 3802 receives the indication and determines that a replaceable strip port module 3801 is connected to the meter 3802, as represented by block 5005.

For example, referring to FIGS. 9 and 10A, when replaceable strip port module 3801 is connected to the analyte meter 3802, the active-low port insertion signal line 3920 is pulled low to indicate to the processor 3810 that a replaceable strip port module 3801 is connected to the analyte meter 3802. Port insertion signal line 3920 is pulled low when pin 10 of connector 4050A, which is tied to grounded pin 9 of connector 4050A, electrically couples with pin 10 of connector 3950.

Referring to FIGS. 9 and 10B, when replaceable strip port module 3801 is connected with the analyte meter 3802, port insertion signal line 3920 is pulled low to indicate to the processor 3810 that a strip port module 3801 is connected to the analyte meter 3802. Port insertion signal line 3920 is pulled low when pin 10 of connector 4050B, which is tied to grounded pin 9 of connector 4050B, electrically couples with pin 10 of connector 3950.

At block 5010, analyte meter 3802 determines the type of replaceable strip port module that is connected when it receives the indication of the type of strip port module from the strip port module 3801. For example, referring to FIGS. 9 and 10A, the first type of replaceable strip port module 3801 pulls the active-low port-type signal line 3913 low to indicate to processor 3810 that the strip port module 3801 is the first type of strip port module 3801. Port type signal line 3913 is pulled low when pin 3 of connector 4050A, which is tied to grounded pin 9 of connector 4050A, electrically couples with pin 3 of connector 3950.

Referring to FIGS. 9 and 10B, the second type of replaceable strip port module 3801 keeps port type signal line 3913 high when the replaceable strip port module 3801 is connected to the analyte meter 3802, which indicates to processor 3810 that the strip port module 3801 is a second type of strip port module. Port type signal line 3913 stays high because pin 3 of connector 4050A is left floating and thus does not affect the signal on port-type signal line 3913.

After receiving an indication of an analyte to be measured, the analyte meter 3802 determines the type of analyte that is to be measured, as represented by block 5015. The replaceable strip port 3801 provides an analyte-type signal to the analyte meter 3802 to indicate the analyte that is to be measured. For example, referring to FIGS. 9 and 10A, when a glucose test strip is inserted into strip port 3820A, replaceable strip port module 3801 pulls the active-low analyte-type signal line 3911 low to indicate to processor 3810 that glucose is to be measured. For instance, a glucose test strip may include an electrical contact that electrically couples grounded pin 9 of strip port 3820A to pin 1 of strip port 3820A when inserted into the strip port 3820A. Pin 1 of connector 4050A is thus grounded and pulls the active-low analyte-type signal line 3911 low.

When a ketone test strip is inserted into strip port 3820A, replaceable strip port module 3801 pulls the active-low analyte-type signal line 3914 low to indicate to processor 3810 that ketone is to be measured. For instance, a ketone test strip may include an electrical contact that electrically couples pin 4 and 5 of strip port 3820A. Since indicator line 4015A is held low by microprocessor 3810, for instance, analyte-type signal line 4014A is pulled low, as well as analyte-type signal line 3914.

Referring to FIGS. 9 and 10B, when a glucose test strip is inserted into strip port 3820B, replaceable strip port module 3801 pulls the active-low analyte-type signal line 3911 low to indicate to processor 3810 that glucose is to be measured. For instance, a glucose test strip may include an electrical contact that electrically couples grounded pin 5 of strip port 3820B with pin 7 of strip port 3820B when inserted into strip port 3820B. Pin 1 of connectors 4050B and 3950 are thus grounded, pulling analyte-type signal line 3911 low.

When a ketone test strip is inserted into strip port 3820B, replaceable strip port module pulls analyte-type signal line 3914 low to indicate to processor 3810 that ketone is to be measured. For instance, a ketone test strip may include an electrical contact that connects grounded pin 5 of strip port 3820B to pin 4 of strip port 3820B. In this way, pin 4 of connectors 4050B and 3950 are grounded, pulling analyte-type signal line 3914 low.

At block 5020, the analog front end of the analyte meter is configured for the appropriate type of replaceable strip port module 3801 and analyte measurement. For example, processor 3810 may control various switches to the external and internal AFE to appropriately configure the analog front end for the specific type of replaceable strip port module connected and specific analyte to be measured. It should be appreciated that the detection of a test strip being inserted into the replaceable strip port module may be used for other purposes, such as to turn on power to the AFE when a test strip is inserted in order to conserve power.

Figure 12:
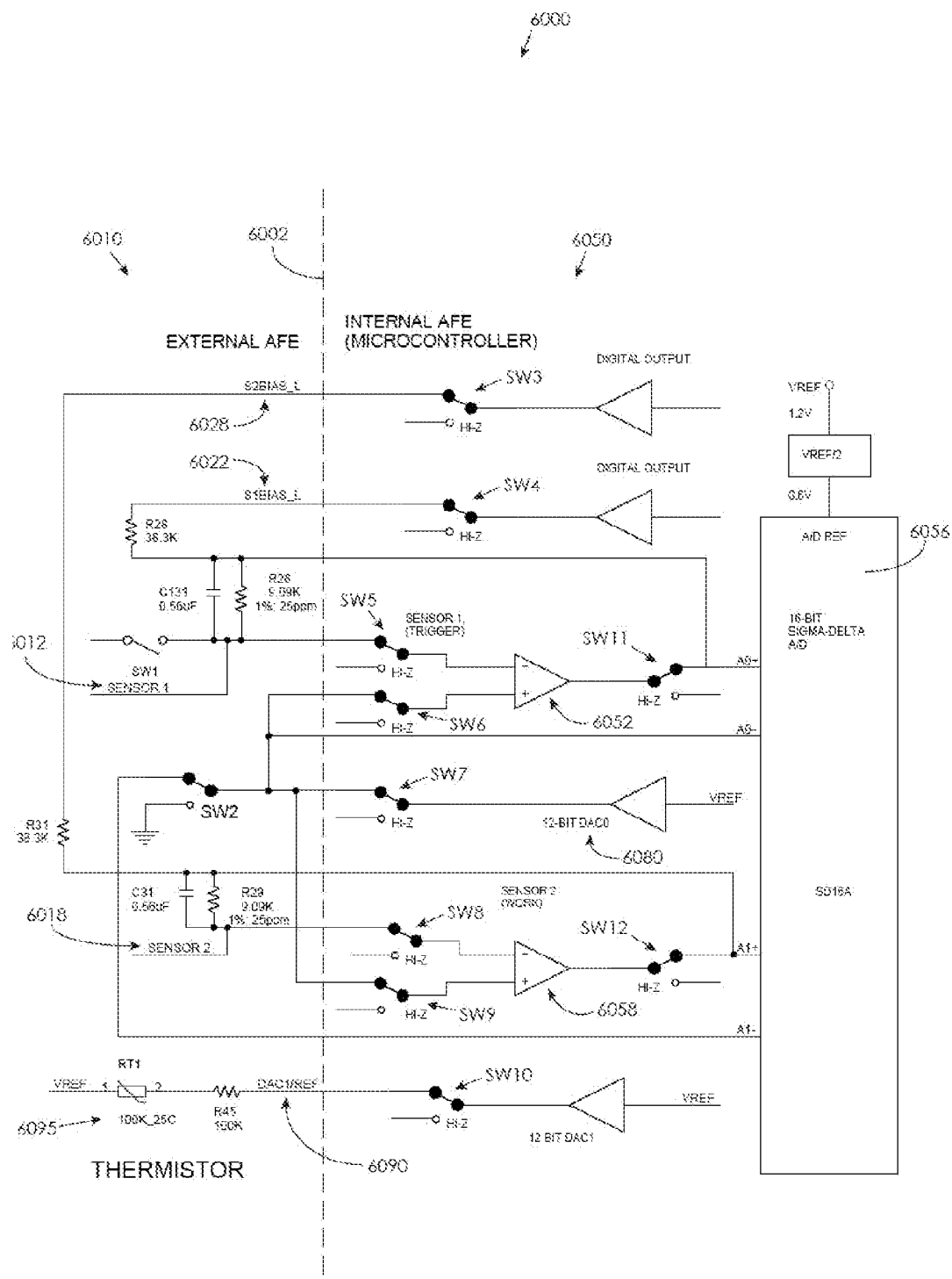
FIG. 12 illustrates an analog front end configuration for a glucose or ketone test measurement when one example type of replaceable strip port module is connected to the analyte meter, according to some embodiments.

Referring to FIGS. 9 and 10B, FIG. 12 illustrates an analog front end configuration for a glucose or ketone test measurement by the second type of replaceable strip port module, according to some embodiments. Analog front end 6000 is shown including front end electronics 6010 external to processor 3810 (also referred to herein as external AFE 6010) and front end electronics 6050 that are internal to processor 3810 (also referred to herein as internal AFE 6050), as represented on opposite sides of dotted line 6002. External AFE 6010 includes switches SW1 and SW2 that are controlled by processor to configure various components of the external AFE. Internal AFE 6010 includes switches SW3, SW4, SW5, SW6, and SW7 that are controlled by processor 3810 to configure various components of the internal AFE. Switches SW3, SW4, SW5, SW6, SW7, SW11, and SW12 enable processor 3810 to use the I/O for different functions.

When the second type of replaceable strip port module connected is indicated to the processor 3810 and the appropriate analyte (e.g., glucose or ketone) to be measured is determined, the processor 3810 configures the analog front end of analyte meter 3802 as shown in FIG. 12. Internal AFE 6050 is shown comprising a sensor amplifier 6052 that functions as a trigger amplifier in this embodiment. The output of trigger amplifier 6052 is input into analog to digital (A/D) converter 6056. Switches SW5, SW6, and SW11 are configured by processor 3810 to activate sensor amplifier 6052—e.g., the inputs and output of the amplifier 6052 are not placed in a high impedance state. Similarly, internal AFE 6050 is shown comprising a sensor amplifier 6058 that functions as a work amplifier in this embodiment. The output of work amplifier 6058 is input into analog to digital (A/D) converter 6056. Switches SW8, SW9, and SW12 are configured by processor 3810 to activate sensor amplifier 6058—e.g., the inputs and output of the amplifier 6058 are not placed in a high impedance state. Switch SW7 is configured to provide reference signal 6080, generated by processor 3810, at the positive inputs of amplifiers 6052 and 6058.

Switch SW4 is configured by processor 3810 to provide biasing signal 6022 to properly bias sensor signal 6012 (e.g., trigger sensor signal) that is input into trigger amplifier 6052. Similarly, switch SW3 is configured by processor 3810 to provide biasing signal 6028 to properly bias the sensor signal 6018 (e.g., work sensor signal) that is input into work amplifier 6058. Switch SW1 is opened to disconnect a portion of circuitry (not shown in FIG. 12) for proper scaling of sensor amplifier 6052. Further, processor 3810 configures SW7 to provide reference signal 6080 to the positive inputs of amplifiers 6052 and 6058. Switch SW10 is configured by processor 3810 to provide a reference signal 6090 for setting the proper measurement of the temperature circuit 6095. Processor 3810 sets switch SW2 as shown for proper measurement of work current with respect to reference signal 6080. As shown, reference signal 6080 is provided into the A1-channel input into the A/D converter 6056.

Referring to FIGS. 9 and 10A, FIG. 13 illustrates an analog front end configuration for a glucose measurement when a first type of replaceable strip port module is connected to the analyte meter, according to some embodiments. When port-type signal line 3913 and analyte-type signal line 3911 are pulled low to indicate the first type of replaceable strip port module and a glucose measurement, the processor 3810 configures the analog front end of analyte meter 3802 accordingly. As shown in FIG. 13 analog front end 6000 is shown including an external AFE 6010 and internal AFE 6050, as represented on opposite sides of dotted line 6002.

Internal AFE 6050 is shown comprising a sensor amplifier 6052 that functions as a work current sensor amplifier in this embodiment. The output of sensor amplifier 6052 is input into analog to digital (A/D) converter 6056. Switches SW5, SW6, and SW11 are configured by processor 3810 to activate sensor amplifier 6052—e.g., the inputs and output of the amplifier 6052 are not placed in a high impedance state. Switch SW7 is configured to provide reference signal 6080, generated by processor 3810, at the positive input of amplifier 6052. Processor 3810 closes switch SW1 to properly scale the work current for the glucose measurement. Switch SW3 is set by processor 3810 so as to provide biasing signal 6022 that biases the sensor signal 6012 that is input into amplifier 6052. Sensor signal 6012 is the current signal obtained from the work sensor, in this embodiment, and provided by sensor signal line 3912 of electrical interface 3816. Switch SW4 is placed in a high impedance state by processor 3810 to disable biasing signal 6028, and is thus not shown in FIG. 13. Moreover, indicator signal 6097 is set low by processor 3810 to enable indicator signal 6096 to be measured with respect to ground. Both signals 6096 and 6097 are provided to indicator signal lines 3917 and 3915 in FIG. 9 into connector 3950, respectively. Switch SW10 is configured by processor to provide a reference signal 6090 that biases the indicator signals lines 3917 and 3915 and work channel. In some embodiments, such as the one shown, the reference signal 6090 is also provided to the temperature circuit 6095 for setting the proper measurement of the temperature circuit 6095. Switch SW2 is configured to provide a ground signal into the A1-channel input into the A/D converter 6056.

Because the second sensor amplifier 6058 is not used with a glucose measurement for the first type of replaceable strip port module, processor 3810 configures switches SW8, SW9, and SW12 at the inputs and output, respectively, of the second amplifier 6058 to disable the second amplifier 6058—e.g., by placing the inputs and outputs of the second amplifier into a high impedance state. The disabling of the second amplifier 6058 also permits the indicator signal 6096 to be measured without interference from the second amplifier 6058. The disabled second amplifier 6058 is not shown in FIG. 13 because it is disabled, but it should be understood that the second sensor is still present but configured to be disabled.

Still referring to FIGS. 9 and 10A, if the analyte-type signal line 3914 is pulled low, a ketone measurement is indicated and processor 3810 configures the analog front end of analyte meter 3802 for a ketone measurement. In such instance, the processor 3810 may configure the AFE such as shown in FIG. 12. For the sake of clarity and brevity, these common features will not be described again, but rather reference is made to the previous discussion of these features.

Referring back to FIG. 11, at block 5030, a measurement may be performed for the specific replaceable strip port module and analyte to be measured. For example, the analyte meter 3802 may perform an analyte measurement for a sample provided by an analyte test strip that has been inserted into strip port 3820 of a connected replaceable strip port module 3801. The resulting analyte level may be presented to the user—e.g., via the display unit on the analyte meter 3802.

Additional Methods

In some aspects, methods are provided for configuring an analyte measurement system based on a replaceable strip port module that releasably connects and operably couples with an analyte meter. The methods comprise providing an analyte meter and replaceable strip port module, such as an analyte meter and a replaceable strip port module described above. The replaceable strip port is then releasably connected to the analyte meter. When connected, the electrical interface on the replaceable strip port module is electrically coupled to the electrical interface on the analyte meter such that an electrical path is formed between the analyte test strip port and the processor. The electrical interface on the replaceable strip port module indicates to the processor, such as described above, that the replaceable strip port module is connected to the meter. In certain embodiments, the indication may be provided to the analyte meter upon connection and without user entry to indicate that the replaceable strip port module is connected. In some instances, the electrical interface on the replaceable strip port module indicates to the processor, such as described above, what type of replaceable strip port module is connected to the meter. In certain embodiments, the indication may be provided to the analyte meter upon connection and without user entry of the type of replaceable strip port module connected. In some instances, when a test strip is inserted into the strip port of the connected replaceable strip port module, the electrical interface on the replaceable strip port module indicates to the processor, such as described above, what type of analyte is to be measured. In certain embodiments, the indication may be provided to the analyte meter upon connection and without user entry of the type of analyte to be measured.

In certain embodiments, the methods may also comprise releasing the replaceable strip port module and then connecting a second replaceable strip port module to the meter. In some instances, the second replaceable strip port module is a different type of replaceable strip port module than the first replaceable strip port module. In some instances, the second replaceable strip port module is the same type of replaceable strip port module than the first replaceable strip port module.

In some aspects, methods are provided for determining a level of an analyte using a measurement system based on a replaceable strip port module that releasably connects and operably couples with an analyte meter. In certain embodiments, the methods may comprise configuring the analyte measurement system, such as described above and represented by blocks 7005, 7010, and 7015 described below, and then performing a measurement using the analyte measurement system.

Figure 14:
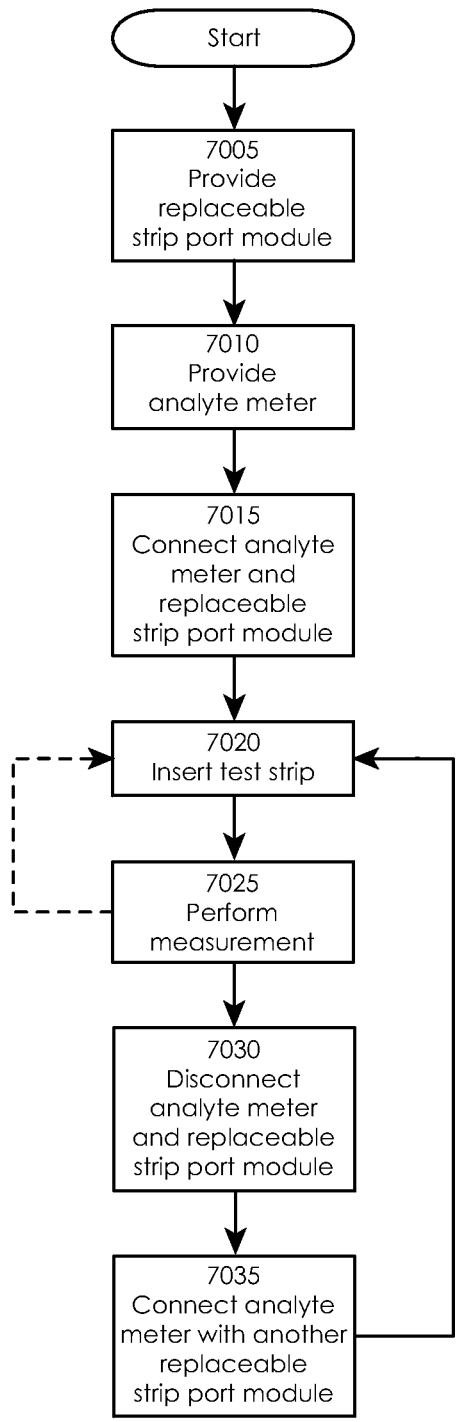
FIG. 14 illustrates a block diagram for a method of determining a level of an analyte, according to certain embodiments.

FIG. 14 illustrates a block diagram for a method of determining a level of an analyte, according to certain embodiments. At block 7005 and 7010, an analyte meter and replaceable strip port module are provided. At block 7015, the replaceable strip port is releasably connected to the analyte meter. When connected, the electrical interface on the replaceable strip port module is electrically coupled to the electrical interface on the analyte meter such that an electrical path is formed between the analyte test strip port and the processor, as described above. The electrical interface on the replaceable strip port module indicates to the processor that the replaceable strip port module is connected to the meter.

At block 7020, an analyte test strip is inserted into the analyte test strip port of the replaceable strip port module. The analyte test strip is a test strip that is compatible with the type of replaceable strip port module. In some instances, one type of replaceable strip port module may be compatible with analyte test strips for different analyte measurements (e.g., compatible with glucose test strips and ketone test strips). At block 7025, a measurement of the analyte level is performed by the analyte meter. The processor may execute one or more algorithm to measure the level of analyte for a sample provided by the test strip. It should be appreciated that the methods may comprise repeating steps 7020 and 7025 multiple times until, for example, the user removes the replaceable strip port module—e.g., to clean, dispose of, or simply replace with another replaceable strip port module, as represented by the dotted line from block 7025 to 7020. In some instances, subsequent analyte test strips are analyte test strips that measure a different type of analyte than the first analyte test strip that was inserted. In some instances, the methods comprise displaying an analyte level on a display unit of the analyte meter and/or audibly presenting the analyte level to the user.

In certain embodiments, as represented at blocks 7030 and 7035, the methods may also comprise releasing the replaceable strip port module and then connecting a second replaceable strip port module to the meter. Another analyte test strip may then inserted into the analyte test strip port of the second replaceable strip port module, and a measurement of the analyte level performed, as represented by the arrow back to block 7020. In some instances, the analyte measured is glucose or a ketone body. In some instances, the second replaceable strip port module is a different type of replaceable strip port module than the first replaceable strip port module. In some instances, the second replaceable strip port module is the same type of replaceable strip port module than the first replaceable strip port module.

Kits

Also provided are kits for use in practicing the subject methods, where the kits may include one or more of the above replaceable strip port modules and/or analyte meters, as described above. As such, a kit may include an analyte meter, and may further include one or more replaceable strip port modules. In some instances, a replaceable strip port module may come preloaded on the analyte meter. In some instances, the replaceable strip port modules may come decoupled from the analyte meter.

In some instances, the kit may further include additional components, such as analyte test strips, batteries, protective coverings (e.g., for any exposed electrical interfaces, ports, etc.), etc., which may find use in practicing the subject methods. The analyte test strips may be provided in a separate container, such as a vial, bag, etc. In some instances, more than one type of analyte test strip may be included in the kit.

In addition to above mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Continuous Monitoring Systems

In certain embodiments, the analyte measurement system communicates with in vivo (e.g., continuous monitoring) systems. A continuous monitoring system typically includes a sensor that is worn or placed below the skin, a transmitter that collects glucose information from the sensor, and a receiver that collects the information from the transmitter. The sensor can collect glucose level information continuously, periodically, or at other intervals. Advantageously, a user is relieved from having to repeatedly lance his or her body to collect a blood sample once the sensor is inserted, although the sensor (e.g., an electrochemical sensor that is inserted into a body) can be replaced. U.S. Pat. No. 6,175,752, which is hereby incorporated by reference in its entirety, discloses additional examples of a continuous monitoring system.

Analyte Test Strips

Analyte test strips for use with the present devices can be of any kind, size, or shape known to those skilled in the art; for example, FREESTYLE® and FREESTYLE LITE™ test strips, as well as PRECISION™ test strips sold by ABBOTT DIABETES CARE Inc. In addition to the embodiments specifically disclosed herein, the devices of the present disclosure can be configured to work with a wide variety of analyte test strips, e.g., those disclosed in U.S. patent application Ser. No. 11/461,725, filed Aug. 1, 2006; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; U.S. patent application Ser. No. 12/102,374, filed Apr. 14, 2008, and U.S. Patent Application Publication No. 2009/0095625; U.S. Pat. No. 6,616,819; U.S. Pat. No. 6,143,164; U.S. Pat. No. 6,592,745; U.S. Pat. No. 6,071,391 and U.S. Pat. No. 6,893,545; the disclosures of each of which are incorporated by reference herein in their entirety.

Calculation of Medication Dosage

In one embodiment, the analyte measurement system may be configured to measure the blood glucose concentration of a patient and include instructions for a long-acting insulin dosage calculation function. Periodic injection or administration of long-acting insulin may be used to maintain a baseline blood glucose concentration in a patient with Type-1 or Type-2 diabetes. In one aspect, the long-acting medication dosage calculation function may include an algorithm or routine based on the current blood glucose concentration of a diabetic patient, to compare the current measured blood glucose concentration value to a predetermined threshold or an individually tailored threshold as determined by a doctor or other treating professional to determine the appropriate dosage level for maintaining the baseline glucose level. In one embodiment, the long-acting insulin dosage calculation function may be based upon LANTUS® insulin, available from Sanofi-Aventis, also known as insulin glargine. LANTUS® is a long-acting insulin that has up to a 24 hour duration of action. Further information on LANTUS® insulin is available at the website located by placing "www" immediately in front of ".lantus.com". Other types of long-acting insulin include Levemir® insulin available from NovoNordisk (further information is available at the website located by placing "www" immediately in front of ".levemir-us.com". Examples of such embodiments are described in US Published Patent Application No. US2010/01981142, the disclosure of which is incorporated herein by reference in its entirety.

Docking Station

In another embodiment, the analyte measurement system may include a corresponding docking station or one or more other peripheral devices. The docking station may include, among others, a transmitter whereby when the analyte measurement system is docked to the docking station, the analyte measurement system and docking station may communicate over a data network with, for example, a healthcare provider, for the transfer of data or receipt of instructions or new dosage regimens. The docking station transmitter may be configured for transmission protocols including, but not limited to, cellular telephone transmission, such as code division multiple access (CDMA) or Global System for Mobile communications (GSM), internet communication, facsimile communications, and/or telephone communication. In another aspect, the docking station may also be configured to provide power for recharging a rechargeable battery of the analyte measurement system. In another aspect, the docking station may be configured for communication with a personal computer for additional storage, programming, and/or communication.

In another embodiment, a docking station such as described in U.S. Pat. No. 7,077,328 may be employed. As stated above, U.S. Pat. No. 7,077,328 is incorporated herein by reference in its entirety.

Test Strip Ejector

In some embodiments, an analyte measurement system as described herein is configured to include an optional analyte test strip ejector configured to eject an analyte test strip from a test strip port of the analyte measurement system. An analyte test strip ejector may be useful, for example, where it is desirable to eject an analyte test strip containing a sample of bodily fluid, e.g., blood, following an analyte measurement conducted using the analyte measurement system. This allows a user of the analyte measurement system to dispose of the contaminated analyte test strip without touching the analyte test strip.

In some embodiments, the analyte test strip ejector slidably engages a portion of the housing of the analyte measurement system. The analyte test strip ejector may be configured such that upon insertion of an analyte test strip into the test strip port, the analyte test strip ejector is moved rearward with respect to the test strip port and in the direction of insertion. In order to eject the analyte test strip, a user physically moves the analyte test strip ejector forward with respect to the test strip port and in the opposite of the direction of insertion. This movement in-turn exerts force upon the analyte test strip expelling it from the test strip port. Alternatively, the analyte test strip ejector may be configured such that insertion of the analyte test strip into a strip port of the analyte measurement system positions the analyte test strip ejector in a "cocked" position, e.g., by engaging a spring mechanism. The analyte measurement system may include a button, switch, or other suitable mechanism for releasing the cocked ejector from the cocked position such that it ejects the analyte test strip from the strip port of the analyte measurement system. Additional information regarding analyte test strip ejectors is provided in the U.S. patent application Ser. No. 12/695,947, filed on Jan. 28, 2010, and entitled "Universal Test Strip Port."

Splash-Proof Test Strip Port

In some embodiments, an analyte measurement system as described herein is configured to include a contamination resistant test strip port and/or a splash-proof test strip port. In one such embodiment, the test strip port includes one or more sealing members positioned so as to limit and/or prevent internal contamination of the test strip port with fluids and/or particles present in the environment outside the test strip port. In another embodiment, the test strip port includes an internal beveled face which can limit and/or prevent ingress of one or more external contaminants into the internal area of the test strip port.

Additional disclosure and examples of contamination resistant test strip ports are provided in U.S. patent application Ser. No. 12/539,217, filed Aug. 11, 2009, and entitled "Analyte Sensor Ports," the disclosure of which is incorporated by reference herein in its entirety.

In some embodiments, the test strip ports described herein can be configured to work with (e.g., engage with or operate in connection with) additional mechanisms and/or devices designed to limit and/or prevent contamination of the internal areas of the test strip ports themselves or the internal areas of the analyte measurement system into which the test strip ports can be integrated. For example, mechanisms, devices and methods of protecting test strip port openings are described in U.S. Patent Application Publication No. US2008/0234559, and U.S. Patent Application Publication No. US2008/0119709, the disclosure of each of which is incorporated by reference herein in their entirety. Test strip ports according to the present disclosure can also be configured to be replaceable and/or disposable, and/or configured so as to limit and/or prevent contamination of the analyte measurement system in which the test strip port is integrated. Additional description is provided, for example, in U.S. Application Publication No. 2010/0064800, the disclosure of which is incorporated by reference herein it its entirety.

Implanted Analyte Sensor

In some embodiments, an analyte measurement system as described herein may communicate and operate with an implanted or partially implanted analyte sensor, e.g., an implanted or partially implanted glucose sensor (e.g., a continuous glucose sensor). In some embodiments, the analyte measurement system may be configured to communicate with the implanted or partially implanted analyte sensor via Radio Frequency Identification (RFID) and provide for intermittent or periodic interrogation of the implanted analyte sensor. The analyte measurement system may be configured to receive analyte data from the implanted or partially implanted glucose sensor either directly or through an intermediate device, e.g., an RF-powered measurement circuit coupled to an implanted or partially implanted analyte sensor.

Exemplary analyte monitoring systems that may be utilized in connection with the disclosed analyte measurement system include those described in U.S. Pat. No. 7,041,468; U.S. Pat. No. 5,356,786; U.S. Pat. No. 6,175,752; U.S. Pat. No. 6,560,471; U.S. Pat. No. 5,262,035; U.S. Pat. No. 6,881,551; U.S. Pat. No. 6,121,009; U.S. Pat. No. 7,167,818;

U.S. Pat. No. 6,270,455; U.S. Pat. No. 6,161,095; U.S. Pat. No. 5,918,603; U.S. Pat. No. 6,144,837; U.S. Pat. No. 5,601,435; U.S. Pat. No. 5,822,715; U.S. Pat. No. 5,899,855; U.S. Pat. No. 6,071,391; U.S. Pat. No. 6,120,676; U.S. Pat. No. 6,143,164; U.S. Pat. No. 6,299,757; U.S. Pat. No. 6,338,790; U.S. Pat. No. 6,377,894; U.S. Pat. No. 6,600,997; U.S. Pat. No. 6,773,671; U.S. Pat. No. 6,514,460; U.S. Pat. No. 6,592,745; U.S. Pat. No. 5,628,890; U.S. Pat. No. 5,820,551; U.S. Pat. No. 6,736,957; U.S. Pat. No. 4,545,382; U.S. Pat. No. 4,711,245; U.S. Pat. No. 5,509,410; U.S. Pat. No. 6,540,891; U.S. Pat. No. 6,730,200; U.S. Pat. No. 6,764,581; U.S. Pat. No. 6,299,757; U.S. Pat. No. 6,461,496; U.S. Pat. No. 6,503,381; U.S. Pat. No. 6,591,125; U.S. Pat. No. 6,616,819; U.S. Pat. No. 6,618,934; U.S. Pat. No. 6,676,816; U.S. Pat. No. 6,749,740; U.S. Pat. No. 6,893,545; U.S. Pat. No. 6,942,518; U.S. Pat. No. 6,514,718; U.S. Pat. No. 5,264,014; U.S. Pat. No. 5,262,305; U.S. Pat. No. 5,320,715; U.S. Pat. No. 5,593,852; U.S. Pat. No. 6,746,582; U.S. Pat. No. 6,284,478; U.S. Pat. No. 7,299,082; U.S. Patent Application No. 61/149,639, entitled "Compact On-Body Physiological Monitoring Device and Methods Thereof", U.S. patent application Ser. No. 11/461,725, filed Aug. 1, 2006, entitled "Analyte Sensors and Methods"; U.S. patent application Ser. No. 12/495,709, filed Jun. 30, 2009, entitled "Extruded Electrode Structures and Methods of Using Same"; U.S. Patent Application Publication No. US2004/0186365; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; US patent Application Publication No. 2010/0198034; and U.S. provisional application No. 61/149,639 titled "Compact On-Body Physiological Monitoring Device and Methods Thereof", the disclosures of each of which are incorporated herein by reference in their entirety.

Integration with Medication Delivery Devices and/or Systems

In some embodiments, the analyte measurement systems disclosed herein may be included in and/or integrated with, a medication delivery device and/or system, e.g., an insulin pump module, such as an insulin pump or controller module thereof. In some embodiments the analyte measurement system is physically integrated into a medication delivery device. In other embodiments, an analyte measurement system as described herein may be configured to communicate with a medication delivery device or another component of a medication delivery system. Additional information regarding medication delivery devices and/or systems, such as, for example, integrated systems, is provided in U.S. Patent Application Publication No. US2006/0224141, published on Oct. 5, 2006, entitled "Method and System for Providing Integrated Medication Infusion and Analyte Monitoring System", and U.S. Patent Application Publication No. US2004/0254434, published on Dec. 16, 2004, entitled "Glucose Measuring Module and Insulin Pump Combination," the disclosure of each of which is incorporated by reference herein in its entirety. Medication delivery devices which may be provided with analyte measurement system as described herein include, e.g., a needle, syringe, pump, catheter, inhaler, transdermal patch, or combination thereof. In some embodiments, the medication delivery device or system may be in the form of a drug delivery injection pen such as a pen-type injection device incorporated within the housing of an analyte measurement system. Additional information is provided in U.S. Pat. Nos. 5,536,249 and 5,925,021, the disclosures of each of which are incorporated by reference herein in their entirety.

Communication Interface

As discussed previously herein, an analyte measurement system according to the present disclosure can be configured to include a communication interface. In some embodiments, the communication interface includes a receiver and/or transmitter for communicating with a network and/or another device, e.g., a medication delivery device and/or a patient monitoring device, e.g., a continuous glucose monitoring device. In some embodiments, the communication interface is configured for communication with a health management system, such as the CoPilot™ system available from Abbott Diabetes Care Inc., Alameda, Calif.

The communication interface can be configured for wired or wireless communication, including, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

In one embodiment, the communication interface is configured to include one or more communication ports, e.g., physical ports or interfaces such as a USB port, an RS-232 port, or any other suitable electrical connection port to allow data communication between the analyte measurement system and other external devices such as a computer terminal (for example, at a physician's office or in hospital environment), an external medical device, such as an infusion device or including an insulin delivery device, or other devices that are configured for similar complementary data communication.

In one embodiment, the communication interface is configured for infrared communication, Bluetooth® communication, or any other suitable wireless communication protocol to enable the analyte measurement system to communicate with other devices such as infusion devices, analyte monitoring devices, computer terminals and/or networks, communication enabled mobile telephones, personal digital assistants, or any other communication devices which the patient or user of the analyte measurement system may use in conjunction therewith, in managing the treatment of a health condition, such as diabetes.

In one embodiment, the communication interface is configured to provide a connection for data transfer utilizing Internet Protocol (IP) through a cell phone network, Short Message Service (SMS), wireless connection to a personal computer (PC) on a Local Area Network (LAN) which is connected to the internet, or WiFi connection to the internet at a WiFi hotspot.

In one embodiment, the analyte measurement system is configured to wirelessly communicate with a server device via the communication interface, e.g., using a common standard such as 802.11 or Bluetooth® RF protocol, or an IrDA infrared protocol. The server device could be another portable device, such as a smart phone, Personal Digital Assistant (PDA) or notebook computer; or a larger device such as a desktop computer, appliance, etc. In some embodiments, the server device has a display, such as a liquid crystal display (LCD), as well as an input device, such as buttons, a keyboard, mouse or touch-screen. With such an arrangement, the user can control the analyte measurement system indirectly by interacting with the user interface(s) of the server device, which in turn interacts with the analyte measurement system across a wireless link.

In some embodiments, the communication interface is configured to automatically or semi-automatically communicate data stored in the analyte measurement system, e.g., in an optional data storage unit, with a network or server device using one or more of the communication protocols and/or mechanisms described above.

Input Unit

As discussed previously herein, an analyte measurement system according to the present disclosure can be configured to include an input unit and/or input buttons coupled to the housing of the analyte measurement system and in communication with a controller unit and/or processor. In some embodiments, the input unit includes one or more input buttons and/or keys, wherein each input button and/or key is designated for a specific task. Alternatively, or in addition, the input unit may include one or more input buttons and/or keys that can be 'soft buttons' or 'soft keys'. In the case where one or more of the input buttons and/or keys are 'soft buttons' or 'soft keys', these buttons and/or keys may be used for a variety of functions. The variety of functions may be determined based on the current mode of the analyte measurement system, and may be distinguishable to a user by the use of button instructions shown on an optional display unit of the analyte measurement system. Yet another input method may be a touch-sensitive display unit, as described in greater detail below.

In addition, in some embodiments, the input unit is configured such that a user can operate the input unit to adjust time and/or date information, as well as other features or settings associated with the operation of an analyte measurement system.

Display Unit

As discussed previously herein, in some embodiments, an analyte measurement system according to the present disclosure includes an optional display unit or a port for coupling an optional display unit to the analyte measurement system. The display unit is in communication with a control unit and/or processor and displays the analyte test strip signals and/or results determined from the analyte test strip signals including, for example, analyte concentration, rate of change of analyte concentration, and/or the exceeding of a threshold analyte concentration (indicating, for example, hypo- or hyperglycemia).

The display unit can be a dot-matrix display, e.g., a dot-matrix LCD display. In some embodiments, the display unit includes a liquid-crystal display (LCD), thin film transistor liquid crystal display (TFT-LCD), plasma display, light-emitting diode (LED) display, seven-segment display, E-ink (electronic paper) display or combination of two or more of the above. The display unit can be configured to provide, an alphanumeric display, a graphical display, a video display, an audio display, a vibratory output, or combinations thereof. The display can be a color display. In some embodiments, the display is a backlit display.

The display unit can also be configured to provide, for example, information related to a patient's current analyte concentration as well as predictive analyte concentrations, such as trending information.

In some embodiments an input unit and a display unit are integrated into a single unit, for example, the display unit can be configured as a touch sensitive display, e.g., a touch-screen display, where the user may enter information or commands via the display area using, for example, the user's finger, a stylus or any other suitable implement, and where, the touch sensitive display is configured as the user interface in an icon driven environment, for example.

In some embodiments, the display unit does not include a screen designed to display results visually. Instead, in some embodiments the optional display unit is configured to communicate results audibly to a user of the analyte measurement system, e.g., via an integrated speaker, or via separate speakers through a headphone jack or Bluetooth® headset.

Expanding Menu Item for Improved Readability

In some embodiments, the display unit includes a graphical user interface including a plurality of menu items, wherein the display unit is configured to provide clarification with respect to the meaning of a menu item based on a user's response speed with respect to a user input for the menu item. The menu item could take any of a variety of forms, e.g., text, icon, object or combination thereof.

In one embodiment, the graphical user interface includes a menu which in turn includes a plurality of selectable menu items. As a user navigates through the menu, e.g., by highlighting or scrolling through individual menu items, a menu item that is either unreadable or incomprehensible to the user could cause the user to pause over a menu item to be selected. In one embodiment, a choice can be presented to the user, e.g., using a dedicated physical button on an input unit, or a soft key on the menu, that offers further explanation of the item to be selected without actually selecting the item. For example, the graphical user interface can be configured such that after a pre-determined period of time a soft key offers an explanation of the menu item to be selected, e.g., by displaying a soft key with the word "MORE", "ADDITIONAL INFORMATION", "EXPAND", "MAGNIFY", "HELP" or a variation thereof displayed thereon.

The pre-determined period of time may be based on a fixed factory preset value, a value set by the user or a health care provider, or through an adaptive mechanism based on an analysis of the user's speed of navigation from past interactions with the graphical user interface. In one embodiment, the pre-determined period of time is from about 5 to about 20 seconds, e.g., from about 10 to about 15 seconds.

If the offer for clarification and/or additional information is selected, e.g., by pressing the softkey, then the menu item to be selected can be displayed in a "high emphasis" mode, e.g., where the item is displayed as if a magnifying lens is held on top of the selected item. In some embodiments, additional emphasis of the menu item to be selected can be provided, e.g., by making the menu item change color, blink, or increase in size to a pre-determined maximum limit.

Support for On-Demand Analyte Determination Using an Analyte Sensor

In some embodiments, an analyte measurement system according to the present disclosure is further configured to communicate with in vivo (e.g., continuous monitoring) systems. A continuous monitoring system typically includes a sensor that is worn or placed below the skin, a transmitter that collects glucose information, for example, from the sensor, and a receiver that collects the information from the transmitter. The sensor can collect glucose level information continuously, periodically, or at other intervals. Advantageously, a user is relieved from having to repeatedly lance his or her body to collect a blood sample once the sensor is inserted, although the sensor (e.g., an electrochemical sensor that is inserted into a body) can be replaced. U.S. Pat. No.

6,175,752, which is hereby incorporated by reference in its entirety, discloses additional examples of a continuous monitoring system.

Support for On-Demand Analyte Determination Using an Analyte Sensor

In some embodiments, an analyte measurement system according to the present disclosure is further configured to receive analyte concentration data and/or signals indicative of an analyte concentration from an analyte sensor, e.g., an implanted or partially implanted analyte sensor or a radio-frequency (RF)-powered measurement circuit coupled to an implanted or partially implanted analyte sensor. In some embodiments, the analyte sensor is a self-powered analyte sensor. An analyte measurement system according to the present disclosure may include software configured to analyze signals received from the analyte sensor. Additional information related to self-powered analyte sensors and methods of communicating therewith are provided in U.S. Patent Application Publication No. 2010/0213057, the disclosure of which is incorporated by reference herein in its entirety.

Integrated Bar Code

In an embodiment, an analyte measurement system according to the present disclosure is integrated with a barcoding system. The barcoding system may be laser or LED based, and may be used for identification of analyte test strips, patient, health care professional, etc. For example, the analyte measurement system may include a barcode reader disposed in the housing. The housing would further require an internal circuitry and a barcode scan engine for processing of a scan. Additional examples of such a bar coding system is provided in U.S. Pat. No. 7,077,328, which has been incorporated herein by reference in its entirety.

Anti-Microbial Thin Film Cover

In an embodiment, an analyte measurement system according to the present disclosure is provided with an anti-microbial thin film cover. A common problem with many analyte measurement systems is that the housing cracks, degrades, and generally wears down due to the harsh chemicals that are used to disinfect the analyte measurement system in hospital and clinical environments. By placing an anti-microbial plastic film over the analyte measurement system, the life-cycle of the system can be prolonged because the plastic film is subjected to the disinfectants, rather than the system housing itself. When the plastic film begins to degrade, it can be removed and replaced. The plastic film also adds an additional layer of sterility to the system. The plastic film may be transparent, and applied over the display and/or user interface. One side of the plastic film would contain anti-microbial chemistry, while the back side of the plastic film would contain a thin layer of adhesive.

Analytes

A variety of analytes can be detected and quantified using the disclosed analyte measurement system. Analytes that may be determined include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones (e.g., ketone bodies), lactate, oxygen, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined. Assays suitable for determining the concentration of DNA and/or RNA are disclosed in U.S. Pat. No. 6,281,006 and U.S. Pat. No. 6,638,716, the disclosures of each of which are incorporated by reference herein in their entirety.

Conclusion

It should be understood that some of the techniques introduced in the preceding can be implemented by programmable circuitry programmed or configured by software and/or firmware, or they can be implemented entirely by special-purpose "hardwired" circuitry, or in a combination of such forms. Such special-purpose circuitry (if any) can be in the form of, for example, one or more application-specific integrated circuits (ASICS), programmable logic devices (PLDs), field-programmable gate arrays (FPGAs), etc.

Software or firmware implementing the techniques introduced herein may be stored on a machine-readable storage medium and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing took, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc. The term "logic", as used herein, can include, for example, special purpose hardwired circuitry, software and/or firmware in conjunction with programmable circuitry, or a combination thereof.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

What is claimed is:

1. A method of configuring an analyte measurement system based on a replaceable strip port module that releasably connects and operably couples with an analyte meter, the method comprising:
providing an analyte meter configured to releasably connect and operably couple with different types of replaceable strip port modules, the analyte meter comprising:
a meter housing;
a processor coupled to the meter housing; and
a first electrical interface coupled to the meter housing and electrically coupled to the processor, the first electrical interface configured to removably and electrically couple to different types of replaceable strip port modules;

providing a first replaceable strip port module configured to releasably connect and operably couple with the analyte meter, the first replaceable strip port module comprising:
  a module housing;
  an analyte test strip port coupled to the module housing and comprising electrical contacts to contact an analyte test strip; and
  a second electrical interface coupled to the module housing and electrically coupled to the analyte test strip port, the second electrical interface configured to removably and electrically couple with the first electrical interface;
connecting the first replaceable strip port module to the analyte meter;
providing, via the second electrical interface of the replaceable strip port module;
  an indication to the processor of the analyte meter that the first replaceable strip port module is connected to the analyte meter, wherein the indication that the first replaceable strip port module is connected to the analyte meter is provided prior to an analyte test strip being inserted into the analyte test strip port; and
  an indication to the processor of what type of replaceable strip port module is connected to the analyte meter.

2. The method of claim 1, wherein connecting the first replaceable strip port module to the analyte meter comprises a first electrical contact on the second electrical interface electrically engaging a second electrical contact on the first electrical interface to provide a port insertion signal to the processor, the port insertion signal indicating that the replaceable strip port module is connected to the analyte meter.

3. The method of claim 2, wherein the first electrical contact is grounded and the port insertion signal is a ground signal.

4. The method of claim 1, wherein connecting the first replaceable strip port module to the analyte meter comprises a first electrical contact on the second electrical interface electrically engaging a second electrical contact on the first electrical interface to provide a port-type signal to the processor, the port-type signal indicating that a first type of replaceable strip port module is connected to the analyte meter.

5. The method of claim 4, wherein the first electrical contact is grounded and the port-type signal is a ground signal.

6. The method of claim 1, wherein connecting the first replaceable strip port module to the analyte meter comprises a first electrical contact on the second electrical interface electrically engaging a second electrical contact on the first electrical interface, wherein the first electrical contact is floating and maintains an existing signal on the second electrical contact, and wherein the maintaining of the existing signal indicates to the processor that a first type of replaceable strip port module is connected to the analyte meter.

7. The method of claim 1, further comprising:
  inserting a test strip into the test strip port of the replaceable strip port module; and
  providing, via the second electrical interface of the replaceable strip port module, an indication to the processor of what type of analyte is to be measured.

8. The method of claim 7, wherein connecting the first replaceable strip port module to the analyte meter comprises a first electrical contact on the second electrical interface electrically engaging a second electrical contact on the first electrical interface to provide a first analyte-type signal to the processor when a test strip for a first type of analyte is inserted into the analyte test strip port, the first analyte-type signal indicating that the first type of analyte is to be measured.

9. The method of claim 7, wherein the first type of analyte is glucose or a ketone body.

10. The method of claim 8, wherein connecting the first replaceable strip port module to the analyte meter comprises a third electrical contact on the second electrical interface electrically engaging a fourth electrical contact on the first electrical interface to provide a second analyte-type signal to the processor when a test strip for a second type of analyte is inserted into the analyte test strip port, the second analyte-type signal indicating that the second type of analyte is to be measured.

11. The method of claim 10, wherein the first type of analyte is glucose and the second type of analyte is a ketone body.

12. The method of claim 1, further comprising:
  releasing the first replaceable strip port module from the analyte meter;
  connecting a second replaceable strip port module to the analyte meter, wherein the second replaceable strip port module comprises:
    a module housing;
    an analyte test strip port coupled to the module housing and comprising electrical contacts to contact an analyte test strip; and
    a third electrical interface coupled to the module housing and electrically coupled to the analyte test strip port of the second replaceable strip port module, the third electrical interface configured to removably and electrically couple with the first electrical interface; and
  providing, via the third electrical interface of the second replaceable strip port module:
    an indication to the processor of the analyte meter that the second replaceable strip port module is connected to the analyte meter, wherein the indication that the second replaceable strip port module is connected to the analyte meter is provided prior to an analyte test strip being inserted into the analyte test strip port of the second replaceable strip port module; and
    an indication to the processor of what type of replaceable strip port module is connected to the analyte meter.

13. A method of determining an analyte level with a measurement system based on a replaceable strip port module that releasably connects and operably couples with an analyte meter, the method comprising:
  providing an analyte meter configured to releasably connect and operably couple with different types of replaceable strip port modules, the analyte meter comprising:
    a meter housing;
    a processor coupled to the meter housing; and
    a first electrical interface coupled to the meter housing and electrically coupled to the processor, the first electrical interface configured to removably and electrically couple to different types of replaceable strip port modules;

providing a first replaceable strip port module configured to releasably connect and operably couple with the analyte meter, the first replaceable strip port module comprising:
- a module housing;
- an analyte test strip port coupled to the module housing and comprising electrical contacts to contact an analyte test strip; and
- a second electrical interface coupled to the module housing and electrically coupled to the analyte test strip port, the second electrical interface configured to removably and electrically couple with the first electrical interface;

connecting the first replaceable strip port module to the analyte meter;

providing, via the second electrical interface of the replaceable strip port module;
- an indication to the processor of the analyte meter that the first replaceable strip port module is connected to the analyte meter, wherein the indication that the first replaceable strip port module is connected to the analyte meter is provided prior to an analyte test strip being inserted into the analyte test strip port; and
- an indication to the processor of what type of replaceable strip port module is connected to the analyte meter;

inserting a first test strip into the analyte test strip port, the first test strip for measuring a level of a first analyte; and performing a first analyte measurement with the analyte meter.

14. The method of claim 13, wherein the first analyte measurement provides a level of glucose or a ketone body.

15. The method of claim 13, wherein connecting the first replaceable strip port module to the analyte meter comprises a first electrical contact on the second electrical interface electrically engaging a second electrical contact on the first electrical interface to provide a port insertion signal to the processor, the port insertion signal indicating that the replaceable strip port module is connected to the analyte meter.

16. The method of claim 15, wherein the first electrical contact is grounded and the port insertion signal is a ground signal.

17. The method of claim 13, wherein connecting the first replaceable strip port module to the analyte meter comprises a first electrical contact on the second electrical interface electrically engaging a second electrical contact on the first electrical interface to provide a port-type signal to the processor, the port-type signal indicating that a first type of replaceable strip port module is connected to the analyte meter.

18. The method of claim 17, wherein the first electrical contact is grounded and the port-type signal is a ground signal.

19. The method of claim 13, wherein connecting the first replaceable strip port module to the analyte meter comprises a first electrical contact on the second electrical interface electrically engaging a second electrical contact on the first electrical interface, wherein the first electrical contact is floating and maintains an existing signal on the second electrical contact, and wherein the maintaining of the existing signal indicates to the processor that a first type of replaceable strip port module is connected to the analyte meter.

20. The method of claim 13, further comprising:
inserting a test strip into the test strip port of the replaceable strip port module; and
providing, via the second electrical interface of the replaceable strip port module, an indication to the processor of what type of analyte is to be measured.

21. The method of claim 20, wherein connecting the first replaceable strip port module to the analyte meter comprises a first electrical contact on the second electrical interface electrically engaging a second electrical contact on the first electrical interface to provide a first analyte-type signal to the processor when a test strip for a first type of analyte is inserted into the analyte test strip port, the first analyte-type signal indicating that the first type of analyte is to be measured.

22. The method of claim 20, wherein the first type of analyte is glucose or a ketone body.

23. The method of claim 21, wherein connecting the first replaceable strip port module to the analyte meter comprises a third electrical contact on the second electrical interface electrically engaging a fourth electrical contact on the first electrical interface to provide a second analyte-type signal to the processor when a test strip for a second type of analyte is inserted into the analyte test strip port, the second analyte-type signal indicating that the second type of analyte is to be measured.

24. The method of claim 23, wherein the first type of analyte is glucose and the second type of analyte is a ketone body.

25. The method of claim 13, further comprising:
releasing the first replaceable strip port module from the analyte meter;
connecting a second replaceable strip port module to the analyte meter, wherein the second replaceable strip port module comprises:
- a module housing;
- an analyte test strip port coupled to the module housing and comprising electrical contacts to contact an analyte test strip; and
- a third electrical interface coupled to the module housing and electrically coupled to the analyte test strip port of the second replaceable strip port module, the third electrical interface configured to removably and electrically couple with the first electrical interface;

providing, via the third electrical interface of the second replaceable strip port module:
- an indication to the processor of the analyte meter that the second replaceable strip port module is connected to the analyte meter, wherein the indication that the second replaceable strip port module is connected to the analyte meter is provided prior to an analyte test strip being inserted into the analyte test strip port of the second replaceable strip port module; and
- an indication to the processor of what type of replaceable strip port module is connected to the analyte meter;

inserting a second test strip into the analyte test strip port of the second replaceable strip port module; and performing a second analyte measurement with the analyte meter.

* * * * *